United States Patent
Sakurai et al.

(10) Patent No.: US 6,826,033 B2
(45) Date of Patent: Nov. 30, 2004

(54) AMINOALCOHOL DERIVATIVES

(75) Inventors: Minoru Sakurai, Osaka (JP); Kenichi Washizuka, Osaka (JP); Hitoshi Hamashima, Osaka (JP); Yasuyo Tomishima, Osaka (JP); Masashi Imanishi, Osaka (JP); Yutaka Nakajima, Osaka (JP); Hiroaki Ohtake, Osaka (JP); Satoru Kuroda, Osaka (JP); Masayoshi Murata, Osaka (JP); Hiroshi Kayakiri, Osaka (JP); Naoaki Fujii, South San Francisco, CA (US); Kiyoshi Taniguchi, Osaka (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 87 days.

(21) Appl. No.: 10/380,627

(22) PCT Filed: Sep. 19, 2001

(86) PCT No.: PCT/JP01/08155

§ 371 (c)(1),
(2), (4) Date: Mar. 21, 2003

(87) PCT Pub. No.: WO02/24635

PCT Pub. Date: Mar. 28, 2002

(65) Prior Publication Data

US 2004/0037022 A1 Feb. 26, 2004

(30) Foreign Application Priority Data

Sep. 25, 2000 (AU) .............................................. PR0340

(51) Int. Cl.$^7$ .............................................. H01G 9/02
(52) U.S. Cl. .................... 361/505; 361/506; 361/507; 514/332; 514/522; 514/534; 514/510
(58) Field of Search ................ 361/505, 506, 361/507; 514/534, 332, 510, 522, 355, 423, 183; 546/261, 276, 277

(56) References Cited

U.S. PATENT DOCUMENTS

| | | | | |
|---|---|---|---|---|
| 5,968,970 A | * | 10/1999 | Getman et al. | 514/422 |
| 6,093,710 A | * | 7/2000 | Tanaka et al. | 514/183 |
| 6,251,947 B1 | * | 6/2001 | Basarab et al. | 514/624 |
| 6,511,669 B1 | * | 1/2003 | Garnier et al. | 424/401 |
| 2002/0006956 A1 | * | 1/2002 | Taniguchi et al. | 514/510 |

FOREIGN PATENT DOCUMENTS

| | | |
|---|---|---|
| WO | 00 12462 | 3/2000 |
| WO | 00 40560 | 7/2000 |

OTHER PUBLICATIONS

U.S. patent application Ser. No. 10/118,929, Taniguchi et al., filed Apr. 10, 2002.
U.S. patent application Ser. No. 10/181,970, Taniguchi et al., filed Aug. 6, 2002.
U.S. patent application Ser. No. 10/380,627, Sakurai et al., filed Mar. 21, 2003.
U.S. patent application Ser. No. 10/380,627, Sakurai et al., filed Mar. 21, 2003.
U.S. patent application Ser. No. 10/746,267, Taniguchi et al., filed Dec. 29, 2003.

* cited by examiner

Primary Examiner—Chau N. Nguyen
Assistant Examiner—Nguyen T. Ha
(74) Attorney, Agent, or Firm—Oblon, Spivak, McClelland, Maier & Neustadt, P.C.

(57) ABSTRACT

The present invention relates to a compound formula (I) wherein $X_1$ is bond or —O—$CH_2$—, (II) or (III) $R^1$ is hydrogen or an amino protective group, a is phenyl, indolyl or carbazolyl, each of which may be substituted with one or two substituent(s), and B is hydrogen; halogen; lower alkyl; lower alkoxycarbonyl; cyclo(lower)alkyl; or a heterocyclic group, naphthyl, 1,2,3,4-tetrahydronaphthyl, benzyl or phenyl, each of which may be substituted with one or two substituent(s), or a salt thereof. The compound (I) of the present invention and pharmaceutically acceptable salts thereof are useful for the prophylactic and/or the therapeutic treatment of pollakiures or urinary incontinence.

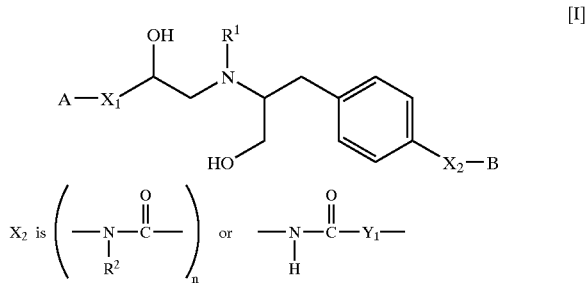

9 Claims, No Drawings

AMINOALCOHOL DERIVATIVES

TECHNICAL FIELD

This invention relates to new aminoalcohol derivatives and salts thereof which are beta-3 ($\beta_3$) adrenergic receptor agonists and useful as a medicament.

DISCLOSURE OF INVENTION

This invention relates to new aminoalcohol derivatives which are $\beta_3$ adrenergic receptor agonists and salts thereof.

More particularly, it relates to new aminoalcohol derivatives and salts thereof which have gut sympathomimetic, anti-ulcerous, anti-pancreatitis, lipolytic, anti-urinary incontinence, anti-pollakiuria activities, anti-diabetes and anti-obesity, to processes for the preparation thereof, to a pharmaceutical composition comprising the same and to a method of using the same therapeutically in the treatment and/or prevention of gastro-intestinal disorders caused by smooth muscle contractions in human beings or animal.

One object of this invention is to provide new and useful aminoalcohol derivatives and salts thereof which have gut sympathomimetic, anti-ulcerous, lipolytic, anti-urinary incontinence, anti-pollakiuria activities, anti-diabetes and anti-obesity.

Another object of this invention is to provide processes for the preparation of said aminoalcohol derivatives and salts thereof.

A further object of this invention is to provide a pharmaceutical composition comprising, as an active ingredient, said aminoalcohol derivatives and salts thereof.

Still further object of this invention is to provide a therapeutical method for the treatment and/or prevention of aforesaid diseases in human beings or animals, using said aminoalcohol derivatives and salts thereof.

The object aminoalcohol derivatives of this invention are new and can be represented by the following formula [I]:

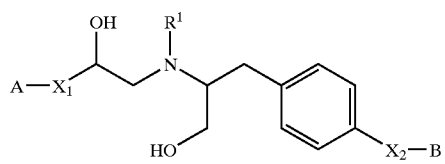

wherein
$X_1$ is bond or —O—CH$_2$—,

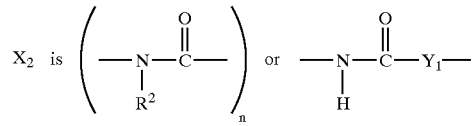

(in which $R^2$ is hydrogen or lower alkyl and n is an integer of 1 or 2)
[in which

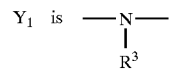

(in which $R^3$ is hydrogen or lower alkyl),

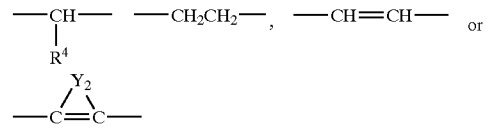

(in which $R^4$ is hydrogen or lower alkyl),
(in which $Y_2$ is lower alkylene)],
$R^1$ is hydrogen or an amino protective group,
A is phenyl, indolyl or carbazolyl, each of which may be substituted with one or two substituent(s) selected from the group consisting of halogen, hydroxy, hydroxy (lower)alkyl and benzyloxy, and
B is hydrogen; halogen; lower alkyl; lower alkoxycarbonyl; cyclo(lower)alkyl; or a heterocyclic group, naphthyl, 1,2,3,4-tetrahydronaphthyl, benzyl or phenyl, each of which may be substituted with one or two substituent(s) selected from the group consisting of halogen, lower alkoxy, mono(or di or tri)halo(lower) alkoxy, carboxy(lower)alkoxy, lower alkoxycarbonyl (lower)alkoxy, phenoxy, lower alkyl, mono(or di or tri)-halo(lower)alkyl, cyano, carboxy, lower alkoxycarbonyl, lower alkanoyl, benzoyl, mono(or di) (lower)-alkylcarbamoyl, (lower alkylsulfonyl) carbamoyl, (lower alkylsulfonyl)amino, (lower alkoxycarbonyl)amino, amino, nitro, pyridyl, triazolyl, thiazolyl optionally substituted with phenyl or lower alkyl, and phenyl optionally substituted with mono(or di or tri)halo(lower)alkyl,
or a salt thereof.

The object compound [I] or a salt thereof can be prepared by the following processes.

Process 1

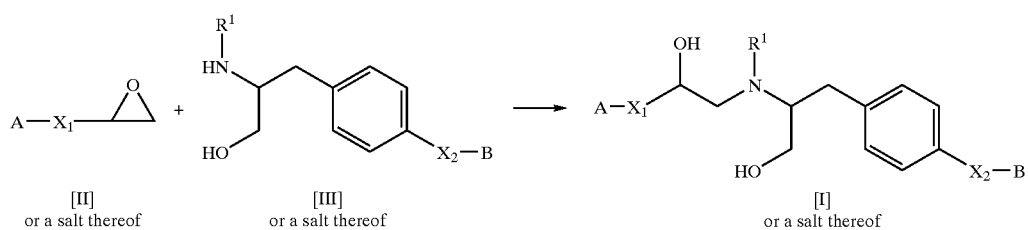

Process 2
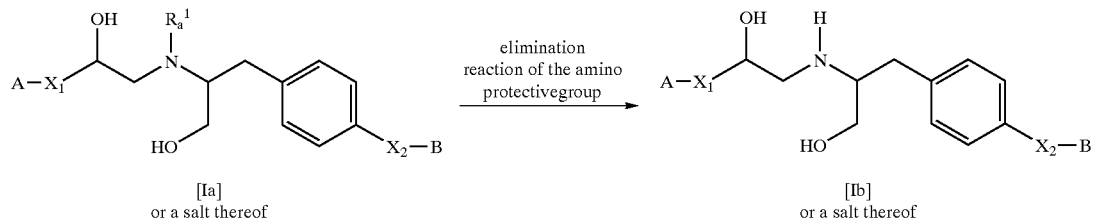
Process 3
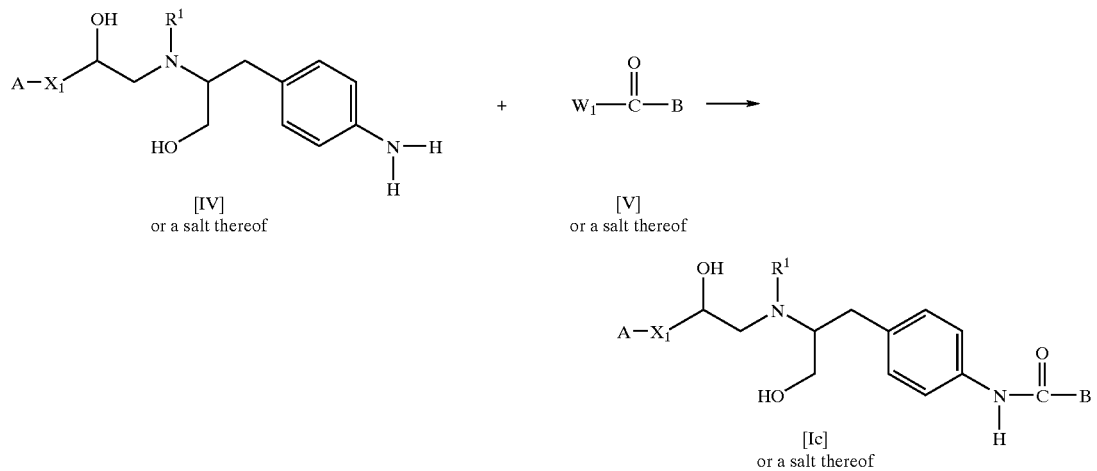
Process 4
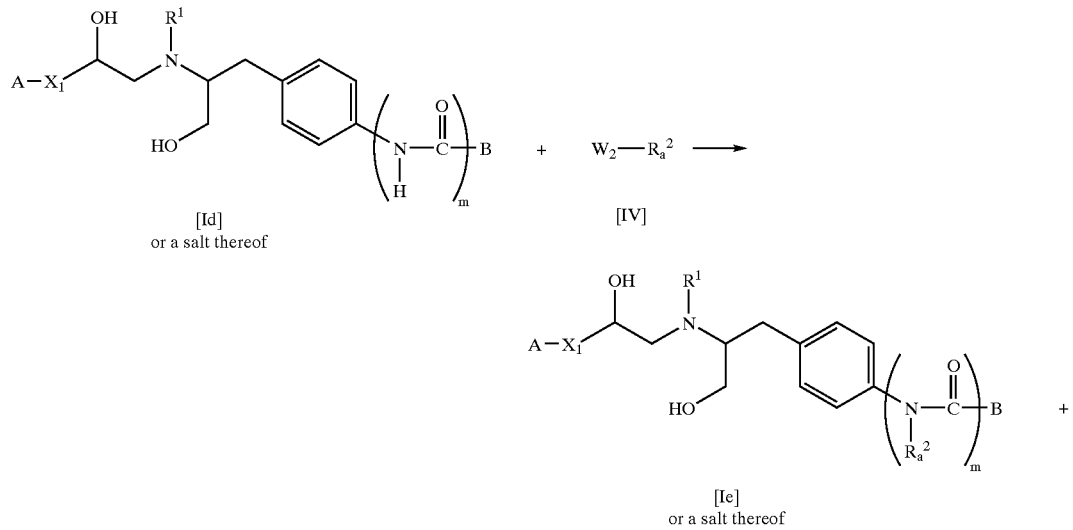
Process 5
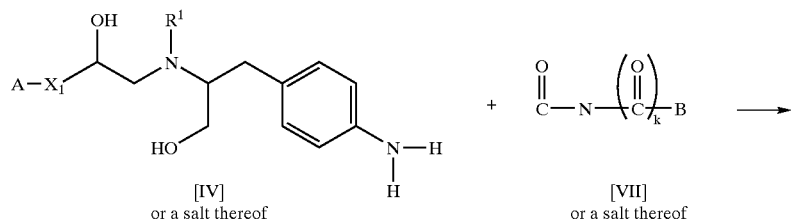

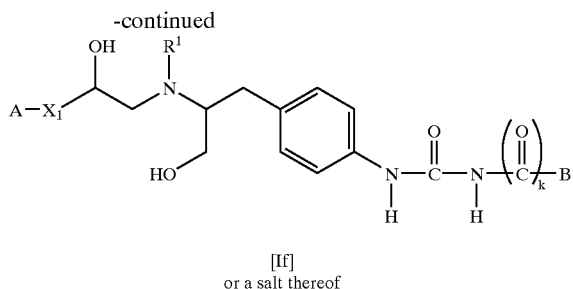

[If]
or a salt thereof

Process 6

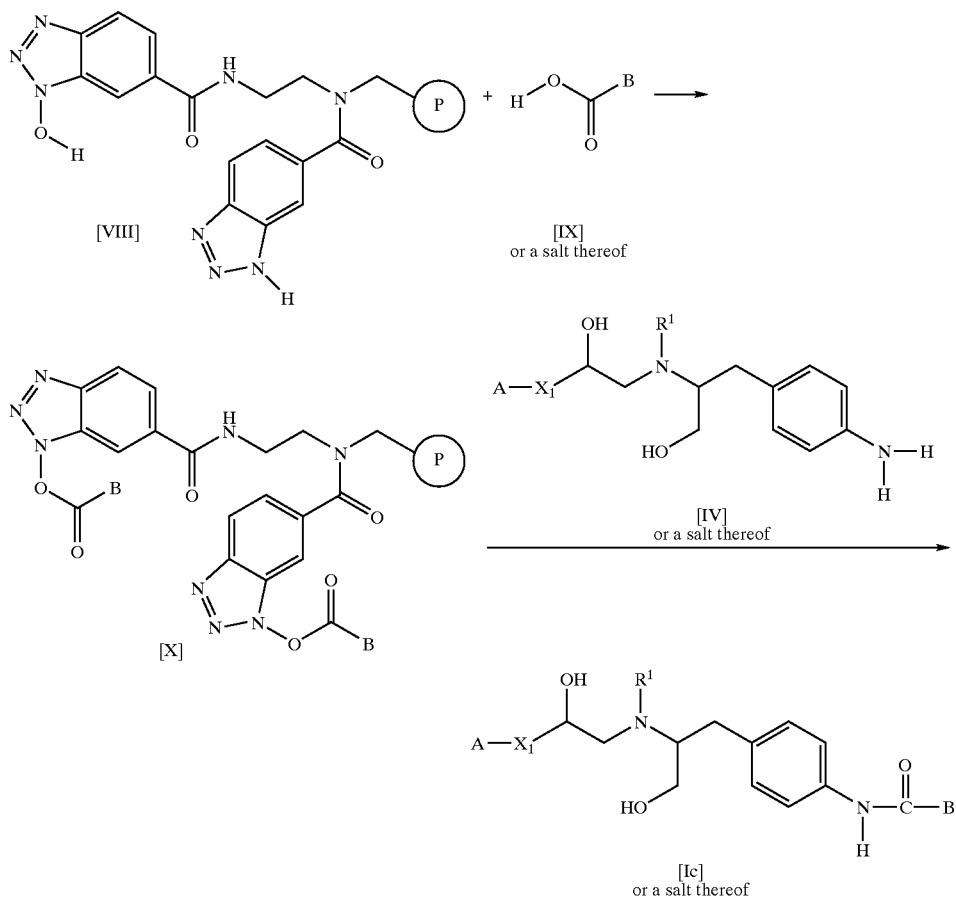

wherein $X_1$, $X_2$, $R^1$, A and B are each as defined above,
$R_a^1$ is an amino protective group,
$R_a^2$ is lower alkyl,
$W_1$ is a leaving group,
$W_2$ is an acid residue,
m is an integer of 1 or 2,
k is 0 or an integer of 1, and
Ⓟ is polymer.

In the above and subsequent description of the present specification, suitable examples of the various definition to be included within the scope of the invention are explained in detail in the following.

The term "lower" is intended to mean a group having 1 to 6, preferably 1 to 4, carbon atom(s), unless otherwise provided.

Suitable example of "lower alkyl" and "lower alkyl" moiety in the terms of "hydroxy(lower)alkyl", "mono(or di or tri)halo(lower)alkyl", etc. may include straight or branched one having 1 to 6 carbon atom(s), such as methyl, ethyl propyl, isopropyl, butyl, isobutyl, sec-butyl, tert-butyl, pentyl, 1-methylpentyl, tert-pentyl, neo-pentyl, hexyl, isohexyl, and the like.

Suitable "lower alkoxy" and "lower alkoxy" moiety in the terms of "lower alkoxycarbonyl", "carboxy(lower)alkoxy", etc. may be a straight or branched one such as methoxy, ethoxy, propoxy, isopropoxy, 1-ethylpropoxy, butoxy, sec-butoxy, tert-butoxy, pentyloxy, neopentyloxy, tert-pentyloxy, hexyloxy, and the like, in which the preferred one may be $C_1$–$C_4$ alkoxy, and the most preferred one may be methoxy or ethoxy.

Suitable "lower alkylene" may include straight or branched one such as methylene, ethylene, trimethylene, tetramethylene, pentamethylene, hexamethylene, methylmethylene, ethylethylene, propylene, and the like, in which more preferable example may be $C_1$–$C_4$ alkylene and the most preferable one may be trimethylene.

Suitable example of "halogen" may be fluoro, chloro, bromo and iodo.

Suitable "cyclo(lower)alkyl" may include cyclopropyl, cyclobutyl, cyclopentyl, and cyclohexyl, in which the preferred one may be cyclohexyl.

Suitable "lower alkanoyl" may be formyl, acetyl, propanoyl, butanoyl, 2-methylpropanoyl, pentanoyl, 2,2-dimethylpropanoyl, hexanoyl and the like, in which the preferred one may be acetyl.

Suitable "mono(or di or tri)halo(lower)alkyl" may be fluoromethyl, difluoromethyl, trifluoromethyl, chloromethyl, dichloromethyl, trichloromethyl, bromomethyl, dibromomethyl, tribromomethyl, 1 or 2-fluoroethyl, 1 or 2-bromoethyl, 1 or 2-chloroethyl, 1,1-difluoroethyl, 2,2-difluoroethyl, and the like, in which the preferred one may be trifluoromethyl.

Suitable example of "heterocyclic group" may include unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, isoquinolyl, phthalazinyl, naphthyridinyl, quinoxalinyl, quinazolinyl, cinnolinyl, indazolyl, benzotriazolyl, etc.;

unsaturated 3 to 8-membered (more preferably 5 or 6-membered) heteromonocyclic group containing 1 or 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 or 2 oxygen atom(s) and 1 to 3 nitrogen atom(s), for example, morpholinyl, sydnonyl, etc.;

unsaturated condensed heterocyclic group containing 1 or 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 or 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 or 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 or 2 sulfur atom(s), for example, thienyl, dihydrodithiinyl, dihydrodithionyl, etc.;

unsaturated condensed heterocyclic group containing 1 or 2 sulfur atom(s) and 1 to 3 nitrogen atom(s), for example, benzothiazolyl, benzothiadiazolyl, imidazothiadiazolyl, etc.;

unsaturated 3 to 8-membered (more preferably 5 or 6-membered) heteromonocyclic group containing an oxygen atom, for example, furyl, etc.;

saturated 3 to 8-membered (more preferably 5 or 6-membered) heteromonocyclic group containing an oxygen atom, for example, tetrahydrofuran, tetrahydropyran, etc.;

unsaturated condensed heterocyclic group containing 1 or 2 oxygen atom(s), for example, benzofuranyl, etc.;

unsaturated 3 to 8-membered (more preferably 5 or 6-membered) heteromonocyclic group containing an oxygen atom and 1 or 2 sulfur atom(s), for example, dihydrooxathiinyl, etc.;

unsaturated condensed heterocyclic group containing 1 or 2 sulfur atom(s), for example, benzothienyl, benzodithiinyl, etc.;

unsaturated condensed heterocyclic group containing an oxygen atom and 1 or 2 sulfur atom(s), for example, benzoxathiinyl, etc.; 2-oxo-2,3-dihydro-1H-benzimidazolyl; and the like.

Suitable example of "polymer" may be polystyrene which may be used for a solid phase support linkage method mentioned below.

Suitable "leaving group" may include hydroxy, reactive group derived from hydroxy and the like.

Suitable "reactive group derived from hydroxy" may include an acid residue and the like.

Suitable "acid residue" may include halogen (e.g. fluoro, chloro, bromo, iodo), acyloxy (e.g. acetoxy, tosyloxy, mesyloxy, etc.) and the like.

Suitable example of "amino protective group" moiety may be common amino protective group such as acyl, for example, substituted or unsubstituted lower alkanoyl [e.g. formyl, acetyl, propionyl, trifluoroacetyl, etc.], phthaloyl, lower alkoxycarbonyl [e.g. tert-butoxycarbonyl, tert-amyloxy-carbonyl, etc.], substituted or unsubstituted aralkyloxy-carbonyl [e.g. benzyloxycarbonyl, p-nitrobenzyloxycarbonyl, etc.], substituted or unsubstituted arenesulfonyl [e.g. benzenesulfonyl, tosyl, etc.], nitrophenylsulfenyl, ar(lower)alkyl [e.g. trityl, benzyl, etc.], and the like, in which preferable one is phenyl(lower)alkyl such as benzyl.

Suitable salts of the object aminoalcohol derivative [I] are pharmaceutically acceptable salts and include conventional non-toxic salts such as an inorganic acid addition salt [e.g. hydrochloride, hydrobromide, sulfate, phosphate, etc.], an organic acid addition salt [e.g. formate, acetate, trifluoroacetate, oxalate, maleate, fumarate, tartarate, citrate, methanesulfonate, benzenesulfonate, toluenesulfonate, etc.] or the like.

The Processes 1 to 5 for preparing the object compound [I] of the present invention are explained in detail in the following.

Process 1

The object compound [I] or a salt thereof can be prepared by reacting a compound [II] or a salt thereof with a compound [III] or a salt thereof.

Suitable salt of the compounds [II] and [III] may be the same as those exemplified for the compound [I].

The reaction is preferably carried out in the presence of a base such as an alkali metal carbonate [e.g. sodium carbonate, potassium carbonate, etc.], an alkaline earth metal carbonate [e.g. magnesium carbonate, calcium carbonate, etc.], an alkali metal bicarbonate [e.g. sodium bicarbonate, potassium bicarbonate, etc.], tri(lower) alkylamine [e.g. trimethylamine, triethylamine, etc.], picoline or the like.

The reaction is usually carried out in a conventional solvent, such as an alcohol [e.g. methanol, ethanol, propanol, isopropanol, etc.], diethyl ether, tetrahydrofuran, dioxane, or any other organic solvent which does not adversely influence the reaction.

The reaction temperature is not critical, and the reaction can be carried out under cooling to heating.

Process 2

The object compound [Ib] or a salt thereof can be prepared by subjecting a compound [Ia] or a salt thereof to elimination reaction of the amino protective group.

Suitable salts of the compounds [Ia] and [Ib] may be the same as those exemplified for the compound [I].

This reaction can be carried out in the manner disclosed in Examples 2 or 11.

Process 3

The object compound [Ic] or a salt thereof can be prepared by reacting the compound [IV] or a salt thereof with the compound [V] or a salt thereof.

Suitable salt of the compounds [Ic], [V] and [IV] may be the same as those exemplified for the compound [I].

This reaction is usually carried out in a solvent such as alcohol [e.g. methanol, ethanol, etc.], dichloromethane, benzene, N,N-dimethylformamide, tetrahydrofuran, diethyl ether or any other solvent which does not adversely affect the reaction.

The reaction may be carried out in the presence of an inorganic or an organic base such as an alkali metal hydroxide [e.g. sodium hydroxide, potassium hydroxide, etc.], an alkali metal carbonate [e.g. sodium carbonate, potassium carbonate, etc.], an alkali metal bicarbonate [e.g. sodium bicarbonate, potassium bicarbonate, etc.], alkali metal hydride [e.g. sodium hydride, potassium hydride, etc.], tri(lower)alkylamine [e.g. trimethylamine, triethylamine, diisopropylethylamine, etc.], pyridine or its derivative [e.g. picoline, lutidine, 4-dimethylaminopyridine, etc.], or the like. In case that the base to be used in liquid, it can also be used as a solvent.

This reaction can be also carried out in the manner disclosed in Example 60, 61 or 62 or similar manners thereto.

The reaction temperature is not critical, and the reaction can be carried out under cooling, at room temperature or under warming or heating.

Process 4

The object compound [Ie] or a salt thereof can be prepared by reacting the compound [Id] or a salt thereof with the compound [VI].

Suitable salt of the compound [Id] and [Ie] may be the same as those exemplified for the compound [I].

This reaction is usually carried out in a conventional solvent such as water, alcohol [e.g. methanol, ethanol, etc.], acetone, dioxane, acetonitrile, chloroform, dichloromethane, ethylene chloride, tetrahydrofuran, ethyl acetate, N,N-dimethylformamide, N,N-dimethylacetamide, pyridine or any other organic solvent which does not adversely influence the reaction.

The reaction temperature is not critical, and the reaction is usually carried out under cooling to warming.

The reaction may also be carried out in the presence of an inorganic or organic base such as an alkali metal bicarbonate, tri(lower)alkylamine (e.g. triethylamine, etc.), pyridine, N-(lower)alkylmorphorine, N,N-di(lower) alkylbenzylamine, or the like.

Process 5

The object compound [If] or a salt thereof can be prepared by subjecting the compound [IV] or a salt thereof with the compound [VII] or a salt thereof.

Suitable salts of the compounds [If], [IV] and [VII] may be the same as those exemplified for the compound [I].

This reaction can be carried out in the manner disclosed in Example 1 or 3 or similar manners thereto.

This reaction can be also carried out in the manner disclosed in Example 64 or 66 or similar manners thereto.

Process 6

The object compound [Ic] or a salt thereof can be prepared by means of a solid phase support linkage method, namely by reacting a compound [VIII] with compound [IX] or a salt thereof and then by reacting the resultant compound [α]with a compound [IV] or a salt thereof.

Suitable salt of the compounds [Ic], [IV], [VIII], [IX] and [α]may be the same as those exemplified for the compound [I].

This reaction can be carried out in the manner disclosed in Example 59 or similar manner thereto.

The compounds obtained by the above processes can be isolated and purified by a conventional method such as pulverization, recrystallization, column chromatography, reprecipitation, or the like, and converted to the desired salt in conventional manners, if necessary.

It is to be noted that the compound [I] and the other compounds may include one or more stereoisomers due to asymmetric carbon atoms, and all of such isomers and mixture thereof are included within the scope of this invention.

It is further to be noted that isomerization or rearrangement of the object compound [I] may occur due to the effect of the light, acid, base or the like, and the compound obtained as the result of said isomerization or rearrangement is also included within the scope of the present invention.

It is also to be noted that the solvating form of the compound [I] (e.g. hydrate, etc.) and any form of the crystal of the compound [I] are included within the scope of the present invention.

The object compound [I] or a salt thereof possesses gut sympathomimetic, anti-ulcerous, anti-pancreatitis, lipolytic, anti-urinary incontinence and anti-pollakiuria activities, and are useful for the treatment and/or prevention of gastrointestinal disorders caused by smooth muscle contractions in human beings or animals, and more particularly for the treatment and/or prevention of spasm or hyperanakinesia in case of irritable bowel syndrome, gastritis, gastric ulcer, duodenal ulcer, enteritis, cholecystopathy, cholangitis, urinary calculus and the like; for the treatment and/or prevention of ulcer such as gastric ulcer, duodenal ulcer, peptic ulcer, ulcer caused by non steroidal anti-inflammatory drugs, or the like; for the treatment and/or prevention of dysuria such as pollakiuria, urinary incontinence or the like in case of nervous pollakiuria, neurogenic bladder dysfunction, nocturia, unstable bladder, cystospasm, chronic cystitis, chronic prostatitis, prostatic hypertrophy or the like; for the treatment and/or prevention of pancreatitis, obesity, diabetes, glycosuria, hyperlipidemia, hypertension, atherosclerosis, glaucoma, melancholia, depression or the like; for the treatment and/or prevention of diseases as the result of insulin resistance (e.g. hypertension, hyperinsulinemia, etc.); for the treatment and/or prevention of neurogenetic inflammation; and for reducing a wasting condition, and the like.

Additionally, $\beta_3$ adrenergic receptor agonists are known to lower triglyceride and cholesterol levels and to raise high density lipoprotein levels in mammals (U.S. Pat. No. 5,451, 677). Accordingly, the object compound [I] is useful in the treatment and/or prevention of conditions such as hypertriglyceridaemia, hypercholesterolaemia and in lowering high density lipoprotein levels as well as in the treatment of atherosclerotic and cardiovascular diseases and related conditions.

Moreover, the object compound [I] is useful for inhibiting uterine contractions, preventing premature labor, and treating and preventing dysmenorrhea.

In order to show the usefulness of the compound [I] for the prophylactic and therapeutic treatment of above-mentioned disease in human beings or animals, the pharmacological test data of a representative compound thereof are shown in the following.

Test

Effect on the increase in intravesical pressure induced by carbachol in anesthetized dog Test Compound (1) N-[4-[(2S)-3-Hydroxy-2-[[(2S)-2-hydroxy-3-phenoxypropyl)amino]propyl]phenyl]-1H-pyrrole-2-carboxamide Test Method Female Beagle dogs weighing 8.0–15.0 kg were fasted for 24 hours and maintained under halothane anesthesia. A 12F Foley catheter was lubricated with water soluble jelly, inserted into the urethral orifice and advanced approximately 10 cm until the balloon tip was placed well inside the bladder. The balloon was then inflated with 5 ml of room air and catheter slowly withdrawn just part the first resistance that is felt at the bladder neck. Urine was completely drained out through the catheter, and 30 ml of biological saline was infused. The catheter was connected to pressure transducer, and intravesical pressure was continuously recorded. The test compound was injected by intra-duodena route at 30 minutes before the administration of carbachol (1.8 $\mu$g/kg).

Test Results

| Treatment | Increase in intravesical pressure (mmHg) |
|---|---|
| Control | 7.0 ± 1.0 |
| Test Compound (1) (0.32 mg/kg) | 2.6 ± 0.05 |

(N = 2)

Preferred embodiments of the object compound [I] are as follow:

$X_1$ is bond or —O—$CH_2$—, $X_2$ is 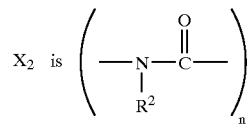

(in which $R^2$ is hydrogen or lower alkyl (more preferably $C_1$–$C_4$ alkyl, most preferably methyl) and n is an integer of 1 or 2)

or 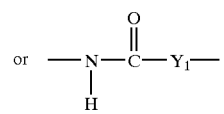

(in which $Y_1$ is

(in which $R^3$ is hydrogen or lower alkyl (more preferably $C_1$–$C_4$ alkyl, most preferably methyl)),

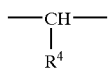

(in which $R^4$ is hydrogen or lower alkyl (more preferably $C_1$–$C_4$ alkyl, most preferably methyl)), —$CH_2CH_2$—, —CH=CH— or

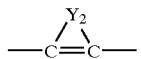

(in which $Y_2$ is lower alkylene (more preferably $C_2$–$C_4$ alkylene, most preferably trimethylene))], $R^1$ is hydrogen, A is phenyl which may be substituted with one or two substituent(s) selected from the group consisting of halogen, hydroxy, hydroxy(lower)alkyl (more preferably hydroxy($C_1$–$C_4$)alkyl, most preferably hydroxymethyl) or benzyloxy, B is pyrrolyl, imidazolyl, pyrazolyl, pyridyl, pyrazinyl, piperidyl, indolyl, benzimidazolyl, quinolyl, isoquinolyl, quinoxalinyl, cinnolinyl, indazolyl, oxazolyl, isoxazolyl, thiazolyl, thienyl, furyl, benzofuranyl, benzothienyl, naphthyl, benzyl or phenyl, each of which may be substituted with one or two substituent(s) selected from the group consisting of halogen (more preferably fluoro or chloro), lower alkoxy (more preferably $C_1$–$C_4$ alkoxy, most preferably methoxy), mono(or di or tri)halo(lower)alkoxy (more preferably mono(or di or tri)($C_1$–$C_4$)alkoxy, most preferably trifluoromethoxy), carboxy(lower)alkoxy (more preferably carboxy($C_1$–$C_4$)alkoxy, most preferably carboxymethoxy), lower alkoxycarbonyl(lower)alkoxy (more preferably $C_1$–$C_4$ alkoxycarbonyl($C_1$–$C_4$) alkoxy, most preferably ethoxycarbonylmethoxy), phenoxy, lower alkyl (more preferably $C_1$–$C_4$ alkyl, most preferably methyl), mono(or di or tri)halo(lower) alkyl (more preferably mono(or di or tri)halo($C_1$–$C_4$) alkyl, most preferably trifluoromethyl), cyano, carboxy, lower alkoxycarbonyl (more preferably $C_1$–$C_4$ alkoxycarbonyl, most preferably ethoxycarbonyl), lower alkanoyl (more preferably $C_1$–$C_4$ alkanoyl, most preferably acetyl), benzoyl, mono(or di)(lower) alkylcarbamoyl (more preferably mono(or di)($C_1$–$C_4$) alkylcarbamoyl, most preferably dimethylcarbamoyl), (lower alkylsulfonyl)carbamoyl(more preferably ($C_1$–$C_4$ alkylsulfonyl)carbamoyl, most preferably (methanesulfonyl)carbamoyl), (lower alkylsulfonyl) amino (more preferably ($C_1$–$C_4$ alkylsulfonyl)amino, most preferably (methanesulfonyl)amino), (lower alkoxycarbonyl)amino (more preferably ($C_1$–$C_4$ alkoxycarbonyl)amino, most preferably (methoxycarbonyl)amino), amino, nitro, pyridyl, triazolyl, thiazolyl optionally substituted with phenyl or lower alkyl (more preferably $C_1$–$C_4$ alkyl, most preferably methyl), and phenyl optionally substituted with mono(or di or tri)halo(lower)alkyl (more preferably mono(or di or tri)halo($C_1$–$C_4$)alkyl, most preferably trifluoromethyl).

More preferred embodiments of the object compound [I] are as follow:

$X_1$ is —O—CH$_2$

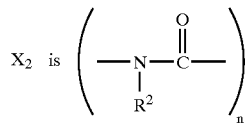

$X_2$ is

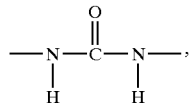

(in which $R^2$ is hydrogen and n is an integer of 1) or $$-\underset{H}{N}-\overset{O}{\underset{\|}{C}}-\underset{H}{N}-,$$

$R^1$ is hydrogen,

A is phenyl which may be substituted with one or two substituent(s) selected from the group consisting of halogen, hydroxy, hydroxy(lower)alkyl and benzyloxy, B is pyrrolyl, pyridyl, naphthyl or phenyl, each of which may be substituted with one or two substituent(s) selected from the group consisting of halogen, lower alkoxy, carboxy(lower)alkoxy, lower alkoxycarbonyl-(lower)alkoxy, lower alkyl, mono(or di or tri)halo-(lower)alkyl, cyano, carboxy, lower alkoxycarbonyl, lower alkanoyl, mono(or di) (lower)alkylcarbamoyl, (lower alkylsulfonyl)carbamoyl, (lower alkylsulfonyl)-amino, (lower alkoxycarbonyl)amino and nitro.

The following Preparations and Examples are given for the purpose of illustrating this invention.

Preparation 1

A mixture of (2S)-2-(phenoxymethyl)oxirane (2.30 g), (2S)-2-amino-3-(4-nitrophenyl)-1-propanol (3.0 g) and ethanol (30 ml) was heated under reflux for 18 hours. The reaction mixture was evaporated in vacuo. The residue was triturated with ethyl acetate to give (2S)-3-(4-nitrophenyl)-2-[((2S)-2-hydroxy-3-phenoxypropyl)amino]-1-propanol (3.97 g) as a pale yellow powder. This powder was used for the next step without further purification.

Preparation 2

A mixture of (2S)-3-(4-nitrophenyl)-2-[((2S)-2-hydroxy-3-phenoxypropyl)amino]-1-propanol (3.97 g), di-tert-butyl dicarbonate (3.0 g) and tetrahydrofuran (40 ml) was stirred at room temperature for 20 hours. The reaction mixture was evaporated in vacuo. The residue was triturated with ether to give tert-butyl N-[(1S)-2-hydroxy-1-(4-nitrobenzyl)-ethyl]-N-((2S)-2-hydroxy-3-phenoxypropyl)carbamate (4.39 g) as a white powder.

NMR (CDCl$_3$, δ): 1.62 (9H, s), 2.15–4.20 (10H, m), 6.78–7.22 (7H, m), 8.18 (2H, d, J=8 Hz)

Preparation 3

A mixture of tert-butyl N-[(1S)-2-hydroxy-1-(4-nitrobenzyl)ethyl]-N-((2S)-2-hydroxy-3-phenoxypropyl)-carbamate (4.29 g), 10% palladium on carbon (50% wet, 429 mg), methanol (43 ml) and tetrahydrofuran (22 ml) was stirred at room temperature under hydrogen atmosphere (1 atm) for 4 hours. The catalyst was removed by vacuum filtration through celite and rinsed with methanol. The filtrate and washings were combined and evaporated in vacuo to give a colorless oil (4.19 g). The residue was purified by a silica gel column chromatography (silica gel 250 g, eluting with hexane:ethyl acetate=1:1) to give the first crop of tert-butyl N-[(1S)-1-(4-aminobenzyl)-2-hydroxyethyl]-N-((2S)-2-hydroxy-3-phenoxypropyl) carbamate (2.85 g) as a colorless syrup and the second crop (527 mg) as a colorless syrup.

NMR (CDCl$_3$, δ): 1.48 (9H, s), 2.40–4.40 (10H, m), 6.62 (2H, d, J=8 Hz), 6.8–7.40 (7H, m)

Preparation 4

A mixture of (2S)-2-amino-3-(4-nitrophenyl)-1-propanol (15.0 g), di-tert-butyl dicarbonate (20.0 g) and tetrahydrofuran (120 ml) was stirred at room temperature for 1.5 hours. The reaction mixture was evaporated in vacuo. The residue was triturated with ether to give tert-butyl N-[(1S)-2-hydroxy-1-(4-nitrobenzyl)ethyl]carbamate (19.82 g) as a white powder.

NMR (CDCl$_3$, δ): 1.40 (9H, s), 2.16 (1H, t, J=4 Hz), 2.98 (2H, d, J=6 Hz), 3.50–3.78 (2H, m), 3.90 (1H, m), 4.82 (1H, d, J=6 Hz), 7.41 (2H, d, J=8 Hz), 8.18 (2H, d, J=8 Hz)

Preparation 5

A mixture of tert-butyl N-[(1S)-2-hydroxy-1-(4-nitrobenzyl)ethyl]carbamate (22.3 g), 2,2-dimethoxypropane (46.3 ml), p-toluenesulfonic acid monohydrate (1.43 g) and dichloromethane (200 ml) was stirred at room temperature for 15 hours. The reaction mixture was washed with saturated aqueous sodium bicarbonate and brine, dried over magnesium sulfate and evaporated in vacuo. The residue was triturated with isopropyl ether to give tert-butyl (S)-4-(4-nitrobenzyl)-2,2-dimethyl-1,3-oxazolidine-3-carboxylate (16.9 g) as a pale yellow powder.

NMR (CDCl$_3$, δ): 1.42–1.68 (15H, m), 2.84 (1H, dd, J=15, 10 Hz), 3.26 (1H, br), 3.72 (1H, d, J=10 Hz), 3.86 (1H, dd, J=10, 7 Hz), 4.10 (1H, br), 7.40 (2H, br), 8.20 (2H, br)

Preparation 6

A mixture of tert-butyl (S)-4-(4-nitrobenzyl)-2,2-dimethyl-1,3-oxazolidine-3-carboxylate (22.25 g), 10% palladium on carbon (50% wet, 2.23 g) methanol (223 ml) and tetrahydrofuran (112 ml) was stirred at room temperature under hydrogen atmosphere (4 atm) for 1.5 hours. The catalyst was removed by vacuum filtration through celite and rinsed with methanol. The filtrate and washings were combined and evaporated in vacuo to give a colorless oil (20.82 g). The residue was purified by a silica gel column chromatography (silica gel 250 g, elution with hexane:ethyl acetate=3:1) to give tert-butyl (S)-4-(4-aminobenzyl)-2,2-dimethyl-1,3-oxazolidine-3-carboxylate as a pale yellow syrup (19.43 g).

NMR (CDCl$_3$, δ): 1.40–1.68 (15H, m), 2.66 (1H, dd, J=12, 10 Hz), 3.06 (1H, br), 3.50–4.04 (3H, m), 7.62 (2H, br d, J=8 Hz), 7.02 (2H, br)

Preparation 7

A suspension of (2S)-2-amino-3-(4-nitrophenyl)-1-propanol (5.89 g) and benzaldehyde (3.39 g) in dichloromethane (59 ml) was stirred at room temperature for 2.5 hours. The mixture was evaporated, and the residual solid was suspended in ethanol (47 ml)-dichloromethane (11.8 ml). Sodium borohydride (1.25 g) was slowly added to the suspension, and the mixture was stirred at room temperature for 5 hours. The mixture was poured onto water (47 ml) and stirred at room temperature for 15 minutes. The precipitate formed was collected by filtration, washed with water, and dried in vacuo. The crude product was recrystallized from ethanol to give (2S)-2-(benzylamino)-3-(4-nitrophenyl)-1-propanol (5.18 g) as a pale yellow powder. The filtrates obtained above were combined, concentrated, and partitioned between chloroform and water. The organic layer was separated, washed successively with water and brine, dried over magnesium sulfate, and filtered. The filtrate was concentrated and the residue was purified by column chromatography (silica gel, chloroform/methanol) to give the additional amount of product (2.78 g) as a white powder.

NMR (CDCl$_3$, δ): 2.72–3.12 (3H, m), 3.35 (1H, dd, J=11 and 4 Hz), 3.64 (1H, dd, J=11 and 4 Hz), 3.80 (2H, s), 7.08–7.48 (7H, m), 8.14 (2H, d, J=9 Hz)

MS m/z: 287 (M$^+$+1)

Preparation 8

A mixture of (2S)-2-(benzylamino)-3-(4-nitrophenyl)-1-propanol (1.15 g) and (2S)-2-(phenoxymethyl)oxirane (661 mg) in ethanol (9.2 ml) was heated to reflux for 3 hours. After allowed to cool to room temperature, the mixture was concentrated and the residue was purified by column chromatography (silica gel, hexane/ethyl acetate) to give (2S)-2-[N-benzyl-N-[(2S)-2-hydroxy-3-phenoxypropyl)amino]-3-(4-nitrophenyl)-1-propanol (1.17 g) as a pale yellow solid.

NMR (CDCl$_3$, δ): 2.60–3.12 (4H, m), 3.12–3.32 (1H, m), 3.40–3.75 (3H, m), 3.75–4.08 (4H, m), 6.84 (2H, d, J=9 Hz), 6.90–7.02 (1H, m), 7.10–7.40 (9H, m), 8.11 (2H, d, J=9 Hz)

MS m/z: 437 (M$^+$+1)

Preparation 9

To a suspension of (2S)-2-[(N-benzyl-N-((2S)-2-hydroxy-3-phenoxypropyl]amino]-3-(4-nitrophenyl)-1-propanol (1.12 g) in ethanol (11 ml)—water (2.2 ml) were added powdered iron (573 mg) and ammonium chloride (55 mg). The mixture was gently heated to reflux for 1 hour and allowed to cool to room temperature. After the insoluble material was filtered off, the filtrate was concentrated and partitioned between chloroform and water. The organic layer was separated, washed successively with water and brine, dried over magnesium sulfate, and filtered. The filtrate was concentrated and the residue was purified by column chromatography (silica gel, hexane/ethyl acetate) to give (2S)-3-(4-aminophenyl)-2-[N-benzyl-N-[(2S)-2-hydroxy-3-phenoxypropyl]amino]-1-propanol (990 mg) as a pale yellow oil.

NMR (CDCl$_3$, δ): 2.44 (1H, dd, J=14 and 9 Hz), 2.70–3.20 (4H, m), 3.42–4.02 (7H, m), 6.61 (2H, d, J=8 Hz), 6.82 (2H, d, J=9 Hz), 6.86–7.02 (3H, m), 7.13–7.40 (7H, m)

MS m/z: 407 (M$^+$+1)

Preparation 10

To a mixture of N-[4-[(2S)-2-[N-benzyl-N-[(2S)-2-hydroxy-3-phenoxypropyl]amino]-3-hydroxypropyl]phenyl]-benzamide (102 mg) and triethylamine (0.1 ml) in dichloromethane (1 ml) was added acetic anhydride (50 μl), and the mixture was stirred at room temperature for 5 hours. The mixture was partitioned between ethyl acetate and water. The organic layer was separated, washed with brine, dried over magnesium sulfate, and filtered. The filtrate was concentrated to give N-[4-[(2S)-3-acetoxy-2-[N-[(2S)-2-acetoxy-3-phenoxypropyl]-N-benzylamino]propyl]phenyl]-benzamide (124 mg) as a white amorphous powder.

NMR (CDCl$_3$, δ): 1.91 (3H, s), 2.04 (3H, s), 2.50–3.40 (5H, m), 3.68–4.24 (6H, m), 4.98–5.20 (1H, m), 6.74–7.02 (3H, m), 7.13 (2H, d, J=9 Hz), 7.16–7.35 (7H, m), 7.42–7.60 (5H, m), 7.77 (1H, br s), 7.80–7.92 (2H, m)

MS m/z: 595 (M$^+$+1)

Preparation 11

To an ice-cooled solution of tert-butyl (S)-4-(4-aminobenzenyl)-2,2-dimethyl-1,3-oxazolidine-3-carboxylate (500 mg) and pyridine (0.16 ml) in dichloromethane (60 ml) was added dropwise benzoyl chloride (0.21 ml). The mixture was stirred at the same temperature for 1 hour and partitioned between chloroform and saturated sodium bicarbonate solution. The organic layer was separated, washed with brine, dried over magnesium sulfate, and filtered. The filtrate was concentrated and the residue was purified by column chromatography (silica gel, hexane/ethyl acetate) to give tert-butyl (S)-4-[4-(benzoylamino)benzyl]-2,2-dimethyl-1,3-oxazolidine-3-carboxylate (690 mg) as colorless oil.

NMR (CDCl$_3$, δ): 2.80–3.00 (2H, m), 3.40–3.80 (3H, m), 7.00–7.50 (9H, m)

MS m/z: 286 (M$^+$+1)

Preparation 12

To a solution of tert-butyl (S)-4-[4-(benzoylamino)benzyl]-2,2-dimethyl-1,3-oxazolidine-3-carboxylate (690 mg) in methanol (20 ml) was added 4N hydrogen chloride in ethyl acetate (5 ml) at room temperature, and the solution was stirred at the same temperature for 4 hours. The mixture was evaporated in vacuo, and the residue was partitioned between chloroform and saturated sodium bicarbonate solution. The organic layer was separated, washed with brine, dried over magnesium sulfate, and filtered. The filtrate was concentrated to give (S)-N-[4-(2-amino-3-hydroxypropyl)phenyl]benzamide (250 mg) as a colorless solid.

NMR (MeOD-d$_4$, δ): 2.95 (2H, d, J=7 Hz), 3.40–3.80 (3H, m), 7.30 (2H, d, J=8 Hz), 7.40–8.00 (7H, m)

MS m/z: 271 (M$^+$+1)

Preparation 13

To an ice-cooled solution of tert-butyl (S)-4-(4-aminobenzyl)-2,2-dimethyl-1,3-oxazolidine-3-carboxylate (1.0 g) in dichloromethane (10 ml) was added dropwise phenyl isocyanate (0.39 ml). The mixture was stirred at the same temperature for 1 hour and partitioned between chloroform and saturated sodium bicarbonate solution. The organic layer was separated, washed with brine, dried over magnesium sulfate, and filtered. The filtrate was concentrated and the residue was purified by column chromatography (silica gel, hexane/ethyl acetate) to give tert-butyl (S)-4-[4-[(anilinocarbonyl)amino]benzyl]-2,2-dimethyl-1,3-oxazolidine-3-carboxylate (1.48 g) as colorless oil.

NMR (CDCl$_3$, δ): 1.50–1.70 (15H, m), 2.60 (1H, dd, J=10, 13 Hz), 3.00–3.20 (1H, m), 3.70–3.80 (2H, m), 4.05–4.10 (1H, m), 6.88–7.40 (9H, m)

Preparation 14

To a solution of tert-butyl (S)-4-[4-[(anilinocarbonyl)amino]benzyl]-2,2-dimethyl-1,3-oxazolidine-3-carboxylate (1.48 g) in methanol (20 ml) was added 4N hydrogen chloride in ethyl acetate (5 ml) at room temperature, and the solution was stirred at the same temperature for 4 hours. The mixture was evaporated in vacuo, and the residue was triturated with diisopropyl ether to give (S)-N-[4-(2-amino-3-hydroxypropyl)phenyl]-N'-phenylurea hydrochloride (660 mg) as a colorless solide.

NMR (MeOD-d$_4$, δ): 2.80–3.00 (2H, m), 3.40–3.80 (3H, m), 7.00–7.50 (9H, m)

MS m/z: 286 (M$^+$+1)

Preparation 15

To a solution of (S)-N-[4-(2-amino-3-hydroxypropyl)phenyl)benzamide (207 mg) and benzaldehyde (106 mg) in 1,4-dioxane (5 ml) was refluxed for 3 hours, and the mixture was evaporated in vacuo. To the residue in methanol (5 ml) was added sodium borohydride (15 mg) on ice-cooling, and stirred at the same temperature for 1 hour. The resulting mixture was poured into saturated aqueous sodium bicarbonate solution, and extracted with ethyl acetate. The organic layer was washed with brine, dried over magnesium sulfate, and evaporated in vacuo. The residue was chromatographed (hexane-ethyl acetate) over silica gel to afford (S)-N-[4-[2-(benzylamino)-3-hydroxypropyl]phenyl]benzamide (250 mg) as colorless oil.

NMR (CDCl$_3$, δ): 2.70–2.83 (2H, m), 2.88–2.98 (1H, m), 3.35 (1H, dd, J=5, 11 Hz), 3.68 (1H, dd, J=4, 11 Hz), 3.79 (2H, s), 7.10–7.90 (14H, m)

MS m/z: 361 (M$^+$+1)

Preparation 16

To an ice-cooled solution of (2S)-1,2-epoxy-3-(3-formyl-4-benzyloxyphenoxy)propane (2.6 g) in methanol (30 ml)

was added sodium borohydride (381 mg). The mixture was stirred at the same temperature for 1 hour and partitioned between chloroform and saturated sodium bicarbonate solution. The organic layer was separated, washed with brine, dried over magnesium sulfate, and filtered. The filtrate was concentrated to give (2S)-1,2-epoxy-3-(3-hydroxymethyl-4-benzyloxyphenoxy)propane (2.57 g) as a yellow oil.

NMR (CDCl$_3$, δ): 2.74 (1H, q, J=3 Hz), 2.89 (1H, t, J=5 Hz), 3.33 (1H, m), 3.92 (2H, dd, J=5, 11 Hz), 4.20 (1H, dd, J=3, 11 Hz), 4.70 (2H, d, J=6 Hz), 5.1 (2H, s), 6.70–7.00 (3H, m), 7.32–7.45 (5H, m)

MS m/z: 309 (M$^+$+Na)

Preparation 17

To a solution of tert-butyl N-[(1S)-1-(4-aminobenzyl)-2-hydroxyethyl]-N-((2S)-2-hydroxy-3-phenoxypropyl) carbamate (200 mg) in 1,2-dichloroethane (2.0 ml) was added N,O-bis(trimethylsilyl)acetamide (119 μl) at room temperature and the solution was stirred for 30 minutes. To the solution was added successively ethyl 2-isocyanatobenzoate (110 mg) and N,N-diisopropylethylamine (8.36 μl) and the mixture was stirred for 2 hours. The reaction mixture was diluted with ethyl acetate (20 ml) and washed with water (20 ml×1) and brine (20 ml×1) successively, dried over magnesium sulfate, and evaporated to give a pale yellow foam. The crude product was purified by a recycling preparative high pressure liquid chromatography equipped with a gel permeation chromatography column (eluent: chloroform) and silica gel chromatography (eluent: hexane/ethyl acetate=2/1) to give ethyl 2-[[[[4-[(2S)-2-[N-(tert-butoxycarbonyl)-N-((2S)-2-hydroxy-3-phenoxypropyl)amino]-3-[(trimethylsilyl)oxy]propyl]phenyl]amino]carbonyl]amino]-benzoate (217 mg) as a white foam.

MS (ESI) m/z: 702 (M+Na$^+$)

Preparation 18

The following compounds were obtained according to a similar manner to that of Preparation 17.

(1) Ethyl 3-[[[[4-[(2S)-2-[(N-(tert-butoxycarbonyl)-N-((2S)-2-hydroxy-3-phenoxypropyl)amino]-3-[(trimethylsilyl)-oxy]propyl]phenyl]amino]carbonyl]amino]benzoate MS (ESI) m/z: 702 (M+Na$^+$)

(2) Ethyl 4-[[[[4-[(2S)-2-[N-(tert-butoxycarbonyl)-N-((2S)-2-hydroxy-3-phenoxypropyl)amino]-3-[(trimethylsilyl)-oxy]propyl]phenyl]amino]carbonyl]amino]benzoate MS (ESI) m/z: 702 (M+Na$^+$)

Preparation 19

To a solution of tert-butyl N-[(1S)-1-(4-aminobenzyl)-2-hydroxyethyl]-N-((2S)-2-hydroxy-3-phenoxypropyl) carbamate (100 mg) in 1,2-dichloroethane (1.0 ml) was added N,O-bis(trimethylsilyl)acetamide (59.3 μl) at room temperature and the solution was stirred for 30 minutes. To the solution was added successively 2-nitrophenyl isocyanate (47.3 mg) and 1.0 M solution of N,N-diisopropylethylamine in 1,2-dichloroethane (24 μl) and the mixture was stirred for 90 minutes. To the mixture was added an additional portion of N,O-bis(trimethylsilyl) acetamide (59.3 μl ) and the whole was stirred overnight. The reaction mixture was diluted with ethyl acetate (20 ml) and washed with water (20 ml×1) and brine (20 ml×1) successively, dried over magnesium sulfate, and evaporated to give a yellow foam. The crude product was purified by a recycling preparative high pressure liquid chromatography equipped with a gel permeation chromatography column (eluent: chloroform) and silica gel chromatography (eluent: hexane/ethyl acetate=4/1) to give tert-butyl N-[(1S)-1-[4-[[[(2-nitrophenyl)-amino]carbonyl]amino]benzyl]-2-[(trimethylsilyl)oxy]ethyl]-N-[(2S)-3-phenoxy-2-[(trimethylsilyl)oxy]propyl]carbamate (100 mg) as a yellow foam.

MS m/z: 747 (M+Na$^+$)

Preparation 20

The following compounds were obtained according to a similar manner to that of Preparation 19.

(1) tert-Butyl N-[(1S)-1-[4-[[[(3-nitrophenyl]amino]-carbonyl]amino]benzyl]-2-[(trimethylsilyl)oxy]ethyl]-N-[(2S)-3-phenoxy-2-[(trimethylsilyl)oxy]propyl] carbamate MS m/z: 747 (MH$^+$)

(2) tert-Butyl N-[(1S)-1-[4-[[[(4-nitrophenyl)amino]-carbonyl]amino]benzyl]-2-[(trimethylsilyl)oxy]ethyl]-N-[(2S)-3-phenoxy-2-[(trimethylsilyl)oxy]propyl] carbamate MS m/z: 747 (MH$^+$)

Preparation 21

To a suspension of (2S)-2-(benzylamino)-3-(4-nitrophenyl)-1-propanol (6.0 g) in ethanol (60 ml) was added (2R)-2-(3-chlorophenyl)oxirane (4.86 g) and the mixture was refluxed for 23 hours. After cooling to room temperature, the solvent was removed by evaporation and the residue was chromatographed on silica gel (eluent: hexane/ethyl acetate=2/1) to give the (2S)-2-[N-benzyl-N-[(2R)-2-(3-chlorophenyl)-2-hydroxyethyl]amino]-3-(4-nitrophenyl)-1-propanol (5.46 g) as a yellow crystalline solid.

MS m/z: 440 (MH$^+$)

Preparation 22

To a solution of (2S)-2-[N-benzyl-N-[(2R)-2-(3-chlorophenyl)-2-hydroxyethyl]amino]-3-(4-nitrophenyl)-1-propanol (5.33 g) in a mixed solvent of methanol (50 ml) and chlorobenzene (50 ml) was added 10% palladium on activated carbon (50% wet, 1.00 g) and the mixture was hydrogenated at 1 atm for 2 hours. The catalyst was filtered off and washed with methanol. The filtrate was concentrated in vacuo to give (2S)-3-(4-aminophenyl)-2-[[(2R)-2-(3-chlorophenyl)-2-hydroxyethyl]amino]-1-propanol dihydrochloride (4.95 g) as a pale yellow solid.

MS m/z: 321 (MH$^+$)

Preparation 23

To a suspension of (2S)-3-(4-aminophenyl)-2-[[(2R)-2-(3-chlorophenyl)-2-hydroxyethyl]amino]-1-propanol dihydrochloride (3.68 g) in a mixed solvent of chloroform and methanol (9:1, 75 ml) was added a saturated aqueous sodium bicarbonate solution (75 ml) and the whole was stirred vigorously. The organic layer was separated and the aqueous layer was extracted with a mixed solvent of chloroform and methanol (9:1, 25 ml×5). The organic layers were combined, dried over magnesium sulfate, filtered, and evaporated to give (2S)-3-(4-aminophenyl)-2-[[(2R)-2-(3-chlorophenyl)-2-hydroxyethyl]amino]-1-propanol (2.78 g) as a pale orange crystalline solid.

Preparation 24

To a solution of (2S)-3-(4-aminophenyl)-2-[[(2R)-2-(3-chlorophenyl)-2-hydroxyethyl]amino]-1-propanol (2.78 g) in tetrahydrofuran (28.0 ml) was added di-tert-butyl dicarbonate (1.99 ml) and the solution was stirred at room temperature for 20 hours. The solvent was removed by evaporation and the residue was chromatographed on silica gel (eluent: hexane/ethyl acetate=1/1) to give tert-butyl N-[(1S)-1-(4-aminobenzyl)-2-hydroxyethyl]-N-[(2R)-2-(3-chlorophenyl)-2-hydroxyethyl]carbamate (1.57 g) as a pale yellow solid.

MS m/z: 443 (M+Na$^+$)

Preparation 25

A solution of (2S)-2-[(4-(benzyloxy)phenoxy)methyl]-oxirane (1.19 g) and (2S)-2-(benzylamino)-3-(4- nitrophenyl)-1-propanol (1.33 g) in ethanol (13 ml) was refluxed for 20 hours. After cooling to room temperature, the solvent was removed by evaporation and the residue was chromatographed on silica gel (eluent: chloroform/methanol=98/2) to give (2S)-2-[N-benzyl-N-[(2S)-3-[4-(benzyloxy)phenoxy]-2-hydroxypropyl]amino]-3-(4-nitrophenyl)-1-propanol (2.04 g) as a yellow gum.

MS m/z: 543 (MH$^+$)

Preparation 26

A solution of (2S)-2-[N-benzyl-N-[(2S)-3-[4-(benzyloxy)phenoxy]-2-hydroxypropyl]amino]-3-(4-nitrophenyl)-1-propanol (2.00 g) in a mixed solvent of ethanol (7.5 ml) and 1,4-dioxane (7.5 ml) was added dropwise to a stirred suspension of iron powder (2.00 g) and ammonium chloride (0.24 g) in a mixed solvent of ethanol (5 ml) and water (5 ml) at 85° C. over 10 minutes and the resulting mixture was stirred at the same temperature for 30 minutes. The insoluble solid was filtered off and washed with dioxane, and the filtrate was concentrated in vacuo. The residue was partitioned between saturated aqueous sodium hydrogencarbonate solution and ethyl acetate. The organic layer was separated, washed with brine, dried over magnesium sulfate, and evaporated to give (2S)-3-(4-aminophenyl)-2-[N-benzyl-N-[(2S)-3-[4-(benzyloxy)phenoxy]-2-hydroxypropyl]-amino]-1-propanol (1.90 g) as a pale yellow oil.

MS m/z: 513 (MH$^+$)

Preparation 27

To a 0.024 M solution of tert-butyl N-[(1S)-1-(4-aminobenzyl)-2-hydroxyethyl]-N-[(2S)-2-hydroxy-3-phenoxypropyl]carbamate in 1,2-dichloromethane (15 ml) was added N,O-bis(trimethylsilyl)acetamide (270 μl) and stirred overnight at ambient temperature. Evaporation of the solvent gave a residue, which was purified by column chromatography on silica gel (eluent: 0–33% ethyl acetate in hexane) to give tert-butyl N-[(1S)-1-(4-aminobenzyl)-2-[(trimethylsilyl)oxy]ethyl]-N-[(2S)-3-phenoxy-2-[(trimethylsilyl)oxy]propylcarbamate (190 mg) as a yellow oil.

NMR (DMSO-d$_6$, δ): 0.02 (9H, s), 0.09 (9H, s), 1.42 (9H, s), 2.55–2.70 (2H, m), 3.20–4.35 (8H, m), 4.87 (2H, s), 6.49 (2H, d, J=8.4 Hz), 6.75–7.00 (5H, m), 7.20–7.35 (2H, m)

(+)-APCI MS m/z: 461 (M-CO$_2$-tert-butyl+H)$^+$

EXAMPLE 1

To an ice-cooled solution of (2S)-3-(4-aminophenyl)-2-[N-benzyl-N-[(2S)-2-hydroxy-3-phenoxypropyl]amino]-1-propanol (83 mg) in dichloromethane (0.8 ml) was added dropwise ethyl isocyanate (0.016 ml). The mixture was stirred at the same temperature for 1.5 hours and partitioned between chloroform and saturated sodium bicarbonate solution. The organic layer was separated, washed with brine, dried over magnesium sulfate, and filtered. The filtrate was concentrated and the residue was purified by column chromatography (silica gel, chloroform/methanol) to give N-[4-[(2S)-2-[N-benzyl-N-[(2S)-2-hydroxy-3-phenoxypropyl]amino]-3-hydroxypropyl]phenyl]-N'-ethylurea (84 mg) as a white amorphous powder.

NMR (CDCl$_3$, δ): 1.12 (3H, t, J=7 Hz), 2.51 (1H, dd, J=14 and 9 Hz), 2.63–3.37 (6H, m), 3.37–4.02 (7H, m), 4.85 (1H, t, J=6 Hz), 6.46 (1H, s), 6.81 (2H, d, J=9 Hz), 6.86–7.40 (12H, m)

MS m/z: 478 (M$^+$+1)

EXAMPLE 2

A solution of N-[4-[(2S)-2-[N-benzyl-N-[(2S)-2-hydroxy-3-phenoxypropyl]amino]-3-hydroxypropyl]phenyl]-N'-ethylurea (73 mg) in methanol (1.5 ml) was hydrogenated (1 atm) over 10% palladium on carbon (11 mg) at room temperature for 12 hours. After the catalyst was filtered off, the filtrate was concentrated and the residue was purified by column chromatography (silica gel, chloroform/methanol) followed by recrystallization from ehtanol/hexane to give N-ethyl-N'-[4-[(2S)-3-hydroxy-2-[[(2S)-2-hydroxy-3-phenoxypropyl]amino]-propyl]phenyl]urea (38 mg) as a white powder.

mp: 129–130° C.

IR (KBr): 1678, 1637, 1597, 1558 cm$^{-1}$

NMR (CD$_3$OD, δ): 1.14 (3H, t, J=7 Hz), 2.62–3.16 (5H, m), 3.21 (2H, q, J=7 Hz), 3.45 (1H, dd, J=1 and 6 Hz), 3.63 (1H, dd, J=11 and 4 Hz), 3.90–4.20 (3H, m), 6.84–7.36 (9H, m)

MS m/z: 388 (M$^+$+1)

EXAMPLE 3

To an ice-cooled solution of (2S)-3-(4-aminophenyl)-2-[N-benzyl-N-[(2S)-2-hydroxy-3-phenoxypropyl]amino]-1-propanol (76 mg) in dichloromethane (0.8 ml) was added dropwise phenyl isocyanate (0.022 ml), and the mixture was stirred at the same temperature for 40 minutes. One drop of 28% ammonia solution was added to the mixture, the mixture was concentrated, and the residue was purified by column chromatography (silica gel, chloroform/methanol) to give N-[4-[(2S)-2-[N-benzyl-N-[(2S)-2-hydroxy-3-phenoxypropyl]-amino]-3-hydroxypropyl]phenyl]-N'-phenylurea (89 mg) as a white amorphous powder.

NMR (CDCl$_3$, δ): 2.48 (1H, dd, J=13 and 8 Hz), 2.63–3.22 (4H, m), 3.38–4.02 (7H, m), 6.66–7.43 (21H, m)

MS m/z: 526 (M$^+$+1)

EXAMPLE 4

The following compounds were obtained according to a similar manner to that of Example 2.

(1) N-[4-[(2S)-3-Hydroxy-2-[[(2S)-2-hydroxy-3-phenoxypropyl]amino]propyl]phenyl]-N'-phenylurea IR (KBr): 3440–2921, 1641, 1596, 1560, 1498, 1315, 1238 cm$^{-1}$ NMR (DMSO-d$_6$, δ): 2.50–2.64 (5H, m), 3.10–3.20 (2H, m), 3.80–4.00 (3H, m), 4.50–4.60 (1H, m), 4.93 (1H, d, J=4.2 Hz), 6.85–7.00 (4H, m), 7.05–7.15 (2H, m), 7.25–7.50 (8H, m), 8.57 (1H, s), 8.63 (1H, s)

MS m/z: 436 (M$^+$+1)

(2) N-[4-[(2S)-3-Hydroxy-2-[[(2S)-2-hydroxy-3-phenoxypropyl]amino]propyl]phenyl]benzamide mp: 124–125° C.

IR (KBr): 1655, 1599, 1529 cm$^{-1}$

NMR (CD$_3$OD, δ): 2.58–3.05 (5H, m), 3.43 (1H, dd, J=11 and 6 Hz), 3.60 (1H, dd, J=11 and 4 Hz), 3.83–4.15 (3H, m), 6.80–7.00 (3H, m), 7.12–7.35 (4H, m), 7.40–7.70 (5H, m), 7.83–8.01 (2H, m)

MS m/z: 421 (M$^+$+1)

(3) N-[4-[(2S)-3-Hydroxy-2-[[(2S)-2-hydroxy-3-phenoxypropyl]amino]propyl]phenyl]-4-methoxybenzamide NMR (CDCl$_3$—CD$_3$OD(1:1), δ): 2.60–3.12 (5H, m), 3.45 (1H, dd, J=11 and 6 Hz), 3.64 (1H, dd, J=11 and 4 Hz), 3.89 (3H, s), 3.90–4.20 (3H, m), 6.80–7.12 (5H, m), 7.12–7.40 (4H, m), 7.60 (2H, d, J=8 Hz), 7.91 (2H, d, J=9 Hz)

MS m/z: 451 (M$^+$+1)

(4) 4–Chloro-N-[4-[(2S)-3-hydroxy-2-[[(2S)-2-hydroxy-3-phenoxypropyl]amino]propyl]phenyl]benzamide NMR (CDCl$_3$—CD$_3$OD(1:1), δ): 2.66–3.15 (5H, m), 3.47 (1H, dd, J=11 and 6 Hz), 3.66 (1H, dd, J=11 and 4 Hz), 3.86–4.20 (3H, m), 6.82–7.06 (3H, m), 7.13–7.38 (4H, m), 7.48 (2H, d, J=8 Hz), 7.62 (2H, d, J=8 Hz), 7.90 (2H, d, J=9 Hz)

MS m/z: 455 (M$^+$+1)

(5) N-[4-[(2S)-3-Hydroxy-2-[[(2S)-2-hydroxy-3-phenoxypropyl]amino]propyl]phenyl]-3-methoxybenzamide NMR (CDCl$_3$—CD$_3$OD(1:1), δ): 2.60–3.10 (5H, m), 3.44 (1H, dd, J=11 and 6 Hz), 3.63 (1H, dd, J=11 and 4 Hz), 3.88 (3H, s), 3.88–4.15 (3H, m), 6.80=7.74 (13H, m)

MS m/z: 451 (M$^+$+1)

(6) 3–Chloro-N-[4-[(2S)-3-hydroxy-2-[[(2S)-2-hydroxy-3-phenoxypropyl]amino]propyl]phenyl]benzamide NMR (CDCl$_3$—CD$_3$OD(1:1), δ): 2.58–3.11 (5H, m), 3.44 (1H, dd, J=11 and 6 Hz), 3.63 (1H, dd, J=11 and 4 Hz), 3.85–4.18 (3H, m), 6.80–8.02 (13H, m)

MS m/z: 455 (M$^+$+1)

(7) N-[4-[(2S)-3-Hydroxy-2-[[(2S)-2-hydroxy-3-phenoxypropyl]amino]propyl]phenyl]-1-naphthamide NMR (CDCl$_3$—CD$_3$OD(1:1), δ): 2.60–3.10 (5H, m), 3.45 (1H, dd, J=11 and 6 Hz), 3.62 (1H, dd, J=11 and 4 Hz), 3.82–4.22 (3H, m), 6.82–8.33 (16H, m)

MS m/z: 471 (M$^+$+1)

(8) N-[4-[(2S)-3-Hydroxy-2-[[(2S)-2-hydroxy-3-phenoxypropyl]amino]propyl]phenyl]-2-naphthamide NMR (CDCl$_3$—CD$_3$OD(1:1), δ): 2.72–3.23 (5H, m), 3.58 (1H, dd, J=11 and 6 Hz), 3.76 (1H, dd, J=11 and 4 Hz), 3.95–4.30 (3H, m), 6.90–8.25 (15H, m), 8.59 (1H, s)

MS m/z: 471 (M$^+$+1)

(9) N-[4-[(2S)-3-Hydroxy-2-[[(2S)-2-hydroxy-3-phenoxypropyl]amino]propyl]phenyl]-1H-pyrrole-2-carboxamide NMR (CDCl$_3$—CD$_3$OD(1:1), δ): 2.76–3.30 (5H, m), 3.63 (1H, dd, J=11 and 6 Hz), 3.82 (1H, dd, J=11 and 4 Hz), 4.03–4.37 (3H, m), 6.39–6.49 (1H, m), 6.98–7.29 (5H, m), 7.29–7.57 (4H, m), 7.76 (2H, d, J=8 Hz)

MS m/z: 410 (M$^+$+1)

(10) N-[4-[(2S)-3-Hydroxy-2-[[(2S)-2-hydroxy-3-phenoxypropyl]amino]propyl]phenyl]nicotinamide NMR (DMSO-d$_6$, δ): 2.53–3.05 (5H, m), 3.29 (1H, dd, J=11 and 6 Hz), 3.44 (1H, dd, J=11 and 4 Hz), 3.76–4.10 (3H, m), 6.80–7.04 (3H, m), 7.13–7.38 (4H, m), 7.57 (1H, dd, J=8 and 5 Hz), 7.70 (2H, d, J=8 Hz), 8.29 (1H, ddd, J=8, 2 and 2 Hz), 8.76 (1H, dd, J=5 and 2 Hz), 9.11 (12H, d, J=2 Hz), 10.45 (1H, br s)

MS m/z: 422 (M$^+$+1)

(11) N-[4-[(2S)-3-Hydroxy-2-[[(2S)-2-hydroxy-3-phenoxypropyl]amino]propyl]phenyl]-N-methylbenzamide mp: 115–116° C.

IR (KBr): 1637, 1601 cm$^{-1}$

NMR (CDCl$_3$, δ): 2.53–3.00 (5H, m), 3.32 (1H, dd, J=11 and 5 Hz), 3.47 (3H, s), 3.58 (1H, dd, J=11 and 4 Hz), 3.84–4.10 (3H, m), 6.80–7.38 (14H, m)

MS m/z: 435 (M$^+$+1)

(12) N-[4-[(2S)-3-Hydroxy-2-[[(2S)-2-hydroxy-3-[4-hydroxy-3-(hydroxymethyl)phenoxy]propyl]amino]propyl]phenyl]-benzamide IR (KBr): 3500–3000, 1641, 1600, 1446, 1029 cm$^{-1}$ NMR (MeOD-d$_4$, δ): 2.90–3.10 (3H, m), 3.30–3.60 (4H, m), 3.80–4.00 (2H, m), 4.10–4.30 (1H, m), 4.71 (2H, s), 6.67 (2H, s), 6.93 (1H, s), 7.10–7.90 (9H, m)

MS m/z: 467 (M$^+$+1)

EXAMPLE 5

To an ice-cooled mixture of (2S)-3-(4-aminophenyl)-2-[N-benzyl-N-[(2S)-2-hydroxy-3-phenoxypropyl]amino]-1-propanol (63 mg) and pyridine (25 µl) in dichloromethane (0.6 ml) was added dropwise benzoyl chloride (22 µl), and the mixture was stirred at room temperature for more than 2 hours. The mixture was partitioned between chloroform-methanol and water. The organic layer was separated, washed with brine, dried over magnesium sulfate, and filtered. The filtrate was concentrated and the residue was purified by column chromatography (silica gel, chloroform/methanol) to give N-[4-[(2S)-2-[N-benzyl-N-[(2S)-2-hydroxy-3-phenoxypropyl]amino]-3-hydroxypropyl]phenyl]benzamide (80 mg) as a white amorphous powder.

NMR (CDCl$_3$, δ): 2.56 (1H, dd, J=14 and 9 Hz), 2.72–3.28 (4H, m), 3.44–4.04 (7H, m), 6.83 (2H, d, J=9 Hz), 6.86–7.03 (1H, m), 7.14 (2H, d, J=8 Hz), 7.20–7.40 (7H, m), 7.40–7.63 (5H, m), 7.78–7.96 (2H, m), 7.80 (1H, br s)

MS m/z: 511 (M$^+$+1)

EXAMPLE 6

To a mixture of (2S)-3-(4-aminophenyl)-2-[N-benzyl-N-[(2S)-2-hydroxy-3-phenoxypropyl]amino]-1-propanol (77 mg) and benzoic acid (28 mg) in N,N-dimethylformamide (0.8 ml) was added 1-[3-(dimethylamino)propyl]-3-ethylcarbodiimide hydrochloride (57 mg), and the mixture was stirred at room temperature for 20 hours. The mixture was partitioned between hexane-ethyl acetate and water. The organic layer was separated, washed successively with water and brine, dried over magnesium sulfate, and filtered. The filtrate was concentrated to give N-[4-[(2S)-2-[N-benzyl-N-[(2S)-2-hydroxy-3-phenoxypropyl]amino)-3-hydroxypropyl]phenyl]-benzamide (95 mg) as a white amorphous powder.

NMR (CDCl$_3$, δ): 2.56 (1H, dd, J=14 and 9 Hz), 2.71–3.28 (4H, m), 3.42–4.03 (7H, m), 6.82 (2H, d, J=9 Hz), 6.88–7.02 (1H, m), 7.14 (2H, d, J=8 Hz), 7.18–7.38 (7H, m), 7.38–7.65 (5H, m), 7.77–7.97 (2H, m), 7.80 (1H, br s)

MS m/z: 511 (M$^+$+1)

EXAMPLE 7

The following compounds were obtained according to a similar manner to that of Example 6.

(1) N-[4-[(2S)-2-[N-Benzyl-N-[(2S)-2-hydroxy-3-phenoxypropyl]amino]-3-hydroxypropyl]phenyl]-4-methoxybenzamide NMR (CDCl$_3$, δ): 2.55 (1H, dd, J=13 and 9 Hz), 2.71–3.26 (4H, m), 3.45–4.02 (7H, m), 3.86 (3H, s), 6.73–7.38 (14H, m), 7.53 (2H, d, J=8 Hz), 7.77 (1H, br s), 7.84 (2H, d, J=9 Hz)

MS m/z: 541 (M$^+$+1)

(2) N-[4-[(2S)-2-[N-Benzyl-N-[(2S)-2-hydroxy-3-phenoxypropyl]amino]-3-hydroxypropyl]phenyl]-4-chlorobenzamide NMR (CDCl$_3$, δ): 2.56 (1H, dd, J=13 and 9 Hz), 2.70–3.28 (4H, m), 3.43–4.05 (7H, m), 6.73–7.03 (3H, m), 7.13 (2H, d, J=9 Hz), 7.17–7.36 (7H, m), 7.46 (2H, d, J=9 Hz), 7.52 (2H, d, J=8 Hz), 7.77 (1H, br s), 7.81 (2H, d, J=9 Hz)

MS m/z: 545 (M$^+$+1)

(3) N-[4-[(2S)-2-[N-Benzyl-N-[(2S)-2-hydroxy-3-phenoxypropyl]amino]-3-hydroxypropyl]phenyl]-3-methoxybenzamide NMR (CDCl$_3$, δ): 2.56 (1H, dd, J=14 and 9 Hz), 2.70–3.30 (4H, m), 3.42–4.03 (7H, m), 3.87 (3H, s), 6.73–7.62 (18H, m), 7.80 (1H, br s)

MS m/z: 541 (M$^+$+1)

(4) N-[4-[(2S)-2-[N-Benzyl-N-[(2S)-2-hydroxy-3-phenoxypropyl]amino]-3-hydroxypropyl]phenyl]-3-chlorobenzamide NMR (CDCl₃, δ): 2.56 (1H, dd, J=14 and 9 Hz), 2.72–3.30 (4H, m), 3.42–4.05 (7H, m), 6.74–7.93 (19H, m)

MS m/z: 545 (M⁺+1)

(5) N-[4-[(2S)-2-[N-Benzyl-N-[(2S)-2-hydroxy-3-phenoxypropyl]amino]-3-hydroxypropyl phenyl]-1-naphthamide NMR (CDCl₃, δ): 2.58 (1H, dd, J=14 and 9 Hz), 2.72–3.28 (4H, m), 3.28–4.03 (7H, m), 6.72–8.04 (21H, m), 8.26–8.45 (1H, m)

MS m/z: 561 (M⁺+1)

(6) N-[4-[(2S)-2-[N-Benzyl-N-[(2S)-2-hydroxy-3-phenoxypropyl]amino]-3-hydroxypropyl]phenyl]-2-naphthamide NMR (CDCl₃, δ): 2.57 (1H, dd, J=14 and 9 Hz), 2.72–3.30 (4H, m), 3.42–4.04 (7H, m), 6.72–8.07 (21H, m), 8.38 (1H, s)

MS m/z: 561 (M⁺+1)

EXAMPLE 8

To a mixture of (2S)-3-(4-aminophenyl)-2-[N-benzyl-N-[(2S)-2-hydroxy-3-phenoxypropyl]amino]-1-propanol (79 mg) and pyrrole-2-carboxylic acid (26 mg) in dichloromethane (0.8 ml) was added 1-[3-(dimethylamino)propyl]-3-ethylcarbodiimide hydrochloride (59 mg), and the mixture was stirred at room temperature for 47 hours. The mixture was partitioned between ethyl acetate and water. The organic layer was separated, washed with brine, dried over magnesium sulfate, and filtered. The filtrate was concentrated, and the residue was purified by column chromatography (silica gel, hexane/ethyl acetate) to give N-[4-[(2S)-2-[N-benzyl-N-[(2S)-2-hydroxy-3-phenoxypropyl]amino]-3-hydroxypropyl]-phenyl]-1H-pyrrole-2-carboxamide (48 mg) as a white amorphous powder.

NMR (CDCl₃, δ): 2.53 (1H, dd, J=14 and 9 Hz), 2.68–3.28 (4H, m), 3.42–4.04 (7H, m), 6.23–6.34 (1H, m), 6.65–6.75 (1H, m), 6.75–7.05 (4H, m), 7.10 (2H, d, J=8 Hz), 7.17–7.41 (7H, m), 7.49 (2H, d, J=8 Hz)₁ 7.58 (1H, br s), 9.56 (1H, br s)

MS m/z: 500 (M⁺+1)

EXAMPLE 9

The following compound was obtained according to a similar manner to that of Example 5.

N-[4-[(2S)-2-[N-Benzyl-N-[(2S)-2-hydroxy-3-phenoxypropyl]amino]-3-hydroxypropyl]phenyl]nicotinamide NMR (CDCl₃, δ): 2.56 (1H, dd, J=14 and 9 Hz), 2.70–3.30 (4H, m), 3.42–4.04 (7H, m), 6.72–7.05 (3H, m), 7.14 (2H, d, J=8 Hz), 7.18–7.38 (7H, m), 7.44 (1H, dd, J=8 and 5 Hz), 7.54 (2H, d, J=8 Hz), 7.98 (1H, br s), 8.21 (1H, ddd, J=8, 2 and 2 Hz), 8.76 (1H, dd, J=5 and 2 Hz), 9.08 (1H, d, J=2 Hz)

MS m/z: 512(M⁺+1)

EXAMPLE 10

To an ice-cooled solution of N-[4-[(2S)-3-acetoxy-2-[N-[(2S)-2-acetoxy-3-phenoxypropyl]-N-benzylamino]propyl]-phenyl]benzamide (107 mg) in tetrahydrofuran (1.1 ml) was added sodium hydride (60% in oil, 17 mg), and the mixture was stirred at the same temperature for 30 minutes. To the mixture was added iodomethane (25 μl), and the mixture was stirred at room temperature for 1.5 hours before being partitioned between ethyl acetate and water. The organic layer was separated, washed with brine, dried over magnesium sulfate, and filtered. The filtrate was concentrated and the residue was dissolved in methanol (1.1 ml)-1,4-dioxane (1.1 ml), then treated with 1N sodium hydroxide (0.5 ml) at room temperature for 1.5 hours. The mixture was concentrated and partitioned between ethyl acetate and water. The organic layer was separated, washed with brine, dried over magnesium sulfate, and filtered. The filtrate was concentrated and the residue was purified by column chromatography (silica gel, hexane/ethyl acetate) to give N-[4-[(2S)-2-[N-benzyl-N-[(2S)-2-hydroxy-3-phenoxypropyl]-amino]-3-hydroxypropyl]phenyl]-N-methylbenzamide (55 mg) as a white amorphous powder.

NMR (CDCl₃, δ): 2.49 (1H, d, J=14 and 9 Hz), 2.65–3.22 (4H, m), 3.34–3.72 (3H, m), 3.47 (3H, s), 3.72–4.04 (4H, m), 6.74–7.40 (19H, m)

MS m/z: 525 (M⁺+1)

EXAMPLE 11

To a 0.5 M solution of tert-butyl N-[(1S)-1-(4-aminobenzyl)-2-hydroxyethyl]-N-((2S)-2-hydroxy-3-phenoxypropyl)carbamate in dichloroethane (40 μl) were added successively 2.0 M solution of N,O-bis(trimethylsilyl)-acetamide in 1-methyl-2-pyrrolidinone (10 μl), 1.0 M solution of ethyl isocyanate in 1-methyl-2-pyrrolidinone (24 μl), and 0.1 M solution of N-ethyldiisopropylamine in 1-methyl-2-pyrrolidinone (20 μl) at room temperature. After shaking at room temperature for 30 minutes, the solution was treated with 500 μl of trifluoroacetic acid/water (95/5) at 50° C. for 30 minutes. The mixture was evaporated and the residue was purified by reverse phase HPLC (0–100% acetonitrile in water (containing 0.1% trifluoroacetic acid)) to give N-[4-[(2S)-3-hydroxy-2-[[(2S)-2-hydroxy-3-phenoxypropyl]amino]propyl]phenyl]-N'-propylurea trifluoroacetate (5.51 mg) as a pale yellow oil.

MS m/z: 402(M⁺+1)

EXAMPLE 12

The following compounds were obtained according to a similar manner to that of Example 11.

(1) N-[4-[(2S)-3-Hydroxy-2-[[(2S)-2-hydroxy-3-phenoxypropyl]amino]propyl]phenyl]-N'-isopropylurea trifluoroacetate MS m/z: 402 (M⁺+1)

(2) N-(2–Chlorophenyl)-N'-[4-[(2S)-3-hydroxy-2-[[(2S)-2-hydroxy-3-phenoxypropyl]amino]propyl]phenyl]urea trifluoroacetate MS m/z: 470 (M⁺+1)

(3) N-[4-[(2S)-3-Hydroxy-2-[[(2S)-2-hydroxy-3-phenoxypropyl]amino]propyl]phenyl]-N'-(3-nitrophenyl)urea trifluoroacetate MS m/z: 450 (M⁺+1)

(4) N-[4-[(2S)-3-Hydroxy-2-[[(2S)-2-hydroxy-3-phenoxypropyl]amino]propyl]phenyl]-N'-(3-methoxyphenyl)urea trifluoroacetate MS m/z: 466 (M⁺+1)

(5) N-Benzoyl-N'-[4-[(2S)-3-hydroxy-2-[[(2S)-2-hydroxy-3-phenoxypropyl]amino]propyl]phenyl]urea trifluoroacetate MS m/z: 464 (M⁺+1)

(6) N-Cyclohexyl-N'-(4-[(2S)-3-hydroxy-2-[[(2S)-2-hydroxy-3-phenoxypropyl]amino]propyl]phenyl]urea trifluoroacetate MS m/z: 442 (M⁺+1)

(7) N-(3-Fluorophenyl)-N'-[4-[(2S)-3-hydroxy-2-[[(2S)-2-hydroxy-3-phenoxypropyl]amino]propyl]phenyl]urea trifluoroacetate
MS m/z: 454 (M$^+$+1)

(8) N-[4-[(2S)-3-Hydroxy-2-[[(2S)-2-hydroxy-3-phenoxypropyl]amino]propyl]phenyl]-N'-4-methoxyphenyl)urea trifluoroacetate
MS m/z: 466 (M$^+$+1)

(9) N-(2–Chloroethyl)-N'-[4-[(2S)-3-hydroxy-2-[[(2S)-2-hydroxy-3-phenoxypropyl)amino]propyl]phenyl]urea trifluoroacetate
MS m/z: 422 (M$^+$+1)

(10) N-(3-Bromophenyl)-N'-[4-[(2S)-3-hydroxy-2-[[(2S)-2-hydroxy-3-phenoxypropyl]amino]propyl]phenyl]urea trifluoroacetate
MS m/z: 515 (M$^+$+1)

(11) N-(4-Bromophenyl)-N'-[4-[(2S)-3-hydroxy-2-[[(2S)-2-hydroxy-3-phenoxypropyl]amino]propyl]phenyl]urea trifluoroacetate
MS m/z: 515 (M$^+$+1)

(12) N-[4-[(2S)-3-Hydroxy-2-[[(2S)-2-hydroxy-3-phenoxypropyl]amino]propyl]phenyl]-N'-(3-methylphenyl)urea trifluoroacetate
MS m/z: 450 (M$^+$+1)

(13) N-[4-[(2S)-3-Hydroxy-2-[[(2S)-2-hydroxy-3-phenoxypropyl]amino]propyl]phenyl]-N'-(2-methylphenyl)urea trifluoroacetate
MS m/z: 450 (M$^+$+1)

(14) N-(3-Acetylphenyl)-N'-[4-[(2S)-3-hydroxy-2-[[(2S)-2-hydroxy-3-phenoxypropyl]amino]propyl]phenyl]urea trifluoroacetate
MS m/z: 478 (M$^+$+1)

(15) N-(3-Cyanophenyl)-N'-[4-[(2S)-3-hydroxy-2-[[(2S)-2-hydroxy-3-phenoxypropyl]amino]propyl]phenyl]urea trifluoroacetate
MS m/z: 461 (M$^+$+1)

(16) Ethyl [[[4-[(2S)-3-hydroxy-2-[[(2S)-2-hydroxy-3-phenoxypropyl]amino]propyl]anilino]carbonyl]amino]-acetate trifluoroacetate
MS m/z: 446 (M$^+$+1)

(17) N-(2,3-Dichlorophenyl)-N'-[4-[(2S)-3-hydroxy-2-[[(2S)-2-hydroxy-3-phenoxypropyl]amino]propyl]phenyl]urea trifluoroacetate
MS m/z: 505 (M$^+$+1)

(18) N-[4–Chloro-3-(trifluoromethyl)phenyl]-N'-[4-[(2S)-3-hydroxy-2-[[(2S)-2-hydroxy-3-phenoxypropyl]amino]-propyl]phenyl]urea trifluoroacetate
MS m/z: 538 (M$^+$+1)

(19) N-(2-Fluorophenyl)-N'-[4-[(2S)-3-hydroxy-2-[[(2S)-2-hydroxy-3-phenoxypropyl)amino]propyl]phenyl]urea trifluoroacetate
MS m/z: 454 (M$^+$+1)

(20) N-(4-Fluorophenyl)-N'-[4-[(2S)-3-hydroxy-2-[[(2S)-2-hydroxy-3-phenoxypropyl]amino]propyl]phenyl]urea trifluoroacetate
MS m/z: 454 (M$^+$+1)

(21) N-(3-Chlorophenyl)-N'-[4-[(2S)-3-hydroxy-2-[[(2S)-2-hydroxy-3-phenoxypropyl]amino]propyl]phenyl]urea trifluoroacetate
MS m/z: 470 (M$^+$+1)

(22) N-[4-[(2S)-3-Hydroxy-2-[[(2S)-2-hydroxy-3-phenoxypropyl]amino]propyl]phenyl]-N'-(2-nitrophenyl) urea trifluoroacetate
MS m/z: 481 (M$^+$+1)

(23) N-[4-[(2S)-3-Hydroxy-2-[[(2S)-2-hydroxy-3-phenoxypropyl]amino]propyl]phenyl]-N'-(4-nitrophenyl) urea trifluoroacetate
MS m/z: 481 (M$^+$+1)

(24) N-[4-[(2S)-3-Hydroxy-2-[[(2S)-2-hydroxy-3-phenoxypropyl]amino]propyl]phenyl]-N'-[2-(trifluoromethyl)phenyl]urea trifluoroacetate
MS m/z: 504 (M$^+$+1)

(25) N-[4-[(2S)-3-Hydroxy-2-[[(2S)-2-hydroxy-3-phenoxypropyl]amino]propyl]phenyl]-N'-[3-(trifluoromethyl)phenyl]urea trifluoroacetate
MS m/z: 504 (M$^+$+1)

(26) N-Benzyl-N'-[4-[(2S)-3-hydroxy-2-[[(2S)-2-hydroxy-3-phenoxypropyl]amino]propyl]phenyl]urea trifluoroacetate
MS m/z: 450 (M$^+$+1)

EXAMPLE 13

To an ice-cooled solution of (2S)-1-phenoxy-3-[N-[(2S)-2-(4-aminophenyl)-1-(hydroxymethyl)ethyl]-N-benzylamino]-2-propanol (95 mg) and pyridine (37 mg) in dichloromethane (1 ml) was added dropwise acetic anhydride (26.2 mg). The mixture was stirred at the same temperature for 1 hour and partitioned between chloroform and saturated sodium bicarbonate solution. The organic layer was separated, washed with brine, dried over magnesium sulfate, and filtered. The filtrate was concentrated. A solution of the residue in methanol (1 ml) was hydrogenated (1 atm) over 10% palladium on carbon (15 mg) at room temperature for 2 hours. After the catalyst was filtered off, the filtrate was concentrated and the residue was purified by column chromatography (silica gel, chloroform/methanol) to give (2S)-1-phenoxy-3-[[(2S)-2-(4-acetamidophenyl)-1-(hydroxymethyl)ethyl]amino]-2-propanol (50 mg) as a colorless form.

IR (KBr): 3300–3200, 1664, 1602, 1407, 1243 cm$^{-1}$

NMR (CDCl$_3$, δ): 2.11 (3H, s), 2.70–3.20 (5H, m), 3.40–3.70 (2H, m), 3.97 (2H, d, J=4.6 Hz), 4.10 (1H, m), 6.80–6.90 (3H, m), 7.10–7.30 (4H, m), 7.48 (2H, d, J=8.5 Hz)

MS m/z: 359 (M$^+$+1)

EXAMPLE 14

The following compound was obtained according to a similar manner to that of Example 13.

(2S)-1-Phenoxy-3-[[(2S)-2-(4-ureidophenyl)-1-(hydroxymethyl)ethyl]amino]-2-propanol IR (KBr): 3500–3200, 1658, 1589, 1548, 1243 cm$^{-1}$ NMR (CDCl$_3$, δ): 2.65–3.00 (5H, m), 3.30–3.80 (2H, m), 3.90–4.05 (3H, m), 6.90–7.40 (9H, m)

MS m/z: 391 (M$^+$+1)

EXAMPLE 15

Under nitrogen, a solution of (S)-N-[4-(2-amino-3-hydroxypropyl)phenyl]-N'-phenylurea hydrochloride (150 mg), (R)-3-chlorostyrene oxide (56 mg) and N,N-diisopropylethylamine (0.17 ml) in ethanol (5 ml) was refluxed for 28 hours. The mixture was evaporated in vacuo. The residue was purified by column chromatography on silica gel (chloroform:methanol=100:1) to give N-[4-[(2S)-2-[[(2R)-2-(3-chlorophenyl)-2-hydroxyethyl]amino]-3-hydroxypropyl]phenyl]-N'-phenylurea (45 mg) as a colorless form.

IR (KBr): 3500–3000, 1648, 1540, 1513, 1313, 1230 cm$^{-1}$

NMR (MeOD-d$_4$, δ): 2.60–2.90 (5H, m), 3.40–3.60 (2H, m), 4.60–4.70 (1H, m), 6.90–7.40 (13H, m)

MS m/z: 440 (M$^+$+1)

EXAMPLE 16

The following compounds were obtained according to a similar manner to that of Example 15.

(1) N-[4-[(2S)-2-[[(2S)-3-(1H-Indol-4-yloxy)-2-hydroxypropyl]amino]-3-hydroxypropyl]phenyl]-N'-phenylurea IR (KBr): 3400–3000, 1644, 1540, 1438, 1228, 1060 cm$^{-1}$ NMR (MeOD-d$_4$, δ): 2.60–3.10 (5H, m), 3.30–3.60 (2H, m), 4.00–4.10 (3H, m), 6.40–6.60 (2H, m), 6.90–7.45 (12H, m)

MS m/z: 475 (M$^+$+1)

(2) N-[4-[(2S)-2-[[(2S)-3-(9H-Carbazol-4-yloxy)-2-hydroxypropyl]amino]-3-hydroxypropyl]phenyl]-N'-phenylurea IR (KBr): 3300–3000, 1637, 1598, 1554, 1504, 1207 cm$^{-1}$ NMR (MeOD-d$_4$, δ): 2.60–3.10 (5H, m), 3.40–3.70 (2H, m), 4.05–4.40 (3H, m), 6.90–7.50 (15H, m), 8.3 (1H, d, J=7 Hz)

MS m/z: 525 (M$^+$+1)

(3) N-[4-[(2S)-2-[[(2S)-3-(4-Fluorophenoxy)-2-hydroxypropyl]amino]-3-hydroxypropyl]phenyl]-N'-phenylurea IR (KBr): 3300–3000, 1637, 1598, 1554, 1504, 1207 cm$^{-1}$ NMR (MeOD-d$_4$, δ): 2.50–2.95 (5H, m), 3.30–3.65 (2H, m), 3.90–4.10 (3H, m), 6.90–7.50 (9H, m)

MS m/z: 454 (M$^+$+1)

(4) N-[4-[(2S)-2-[N-Benzyl-N-[(2S)-3-[4-(benzyloxy)-3-(hydroxymethyl)phenoxy]-2-hydroxypropyl]amino]-3-hydroxypropyl]phenyl]benzamide NMR (CDCl$_3$, δ): 2.30–3.00 (6H, m), 3.05–3.20 (1H, m), 3.40–4.00 (7H, m), 4.60 (2H, d, J=6.4 Hz), 5.00 (2H, s), 6.67 (1H, dd, J=3, 9 Hz), 6.80–6.85 (2H, m), 7.10–7.60 (18H, m), 7.80–7.90 (3H, m)

MS m/z: 647 (M$^+$+1)

EXAMPLE 17

To a solution of 10% hydrogen chloride in methanol was added N-[4-[(2S)-3-hydroxy-2-[[(2S)-2-hydroxy-3-phenoxypropyl]amino)propyl]phenyl]-N'-phenylurea (70 mg) and stirred for 15 minutes. The reaction mixture was concentrated and followed by recrystallization from ethanol to give N-[4-[(2S)-3-hydroxy-2-([(2S)-2-hydroxy-3-phenoxypropyl]amino]propyl]phenyl]-N'-phenylurea hydrochloride (38 mg) as a white powder.

IR (KBr): 3330–2950, 1697, 1600, 1556, 1498, 1319, 1238 cm$^{-1}$

NMR (DMSO-d$_6$, δ): 2.70–3.35 (4H, m), 3.40–3.70 (3H, m) 4.00 (2H, d, J=5.0 Hz), 4.15–4.30 (1H, m), 5.41 (1H, s), 5.87 (1H, d, J=4.8 Hz), 6.90–7.00 (4H, m), 7.15–7.50 (10H, m), 9.06 (1H, s), 9.07 (1H, s)

MS m/z: 436 (M$^+$+1)

EXAMPLE 18

To a solution of ethyl 2-[[[[4-[(2S)-2-[N-(tert-butoxycarbonyl)-N-((2S)-2-hydroxy-3-phenoxypropyl)amino]-3-[(trimethylsilyl)oxy]propyl]phenyl]amino]carbonyl]amino]-benzoate (10.0 mg) in 1,2-dichloroethane (100 µl) was added trifluoroacetic acid (100 µl) and the solution was stirred at room temperature for 30 minutes. The solvent was removed by evaporation to give ethyl 2-[[[[4-[(2S)-3-hydroxy-2-[[(2S)-2-hydroxy-3-phenoxypropyl]amino]propyl]phenyl]amino]-carbonyl]amino]benzoate trifluoroacetate (10.3 mg) as a white foam.

MS m/z: 508 (MH$^+$)

EXAMPLE 19

The following compounds were obtained according to a similar manner to that of Example 18.

(1) Ethyl 3-[[[[4-[(2S)-3-hydroxy-2-[[(2S)-2-hydroxy-3-phenoxypropyl]amino]propyl]phenyl]amino]carbonyl]amino]benzoate trifluoroacetate MS m/z: 508 (MH$^+$)

(2) Ethyl 4-[[[[4-[(2S)-3-hydroxy-2-[[(2S)-2-hydroxy-3-phenoxypropyl]amino]propyl]phenyl]amino]carbonyl]amino]benzoate trifluoroacetate MS m/z: 508 (MH$^+$)

EXAMPLE 20

To a solution of tert-butyl N-[(1S)-1-[4-[[[(2-nitrophenyl)amino]carbonyl]amino]benzyl]-2-(trimethylsilyl)oxy]ethyl]-N-[(2S)-3-phenoxy-2-[(trimethylsilyl)oxy]propyl]carbamate (95.0 mg) in methanol (2.9 ml) was added 10% palladium on activated carbon (50% wet, 95 mg) and the mixture was hydrogenated at 1 atm for 1 hour. The catalyst was filtered off and the filtrate was concentrated in vacuo to give tert-butyl N-[(1S)-1-[4-[[[(2-aminophenyl)amino]carbonyl]amino]benzyl]-2-hydroxyethyl]-N-[(2S)-2-hydroxy-3-phenoxypropyl]carbamate (75.3 mg) as a brown solid.

MS (ESI) m/z: 573 (M+Na$^+$)

EXAMPLE 21

The following compounds were obtained according to a similar manner to that of Example 20.

(1) tert-Butyl N-[(1S)-1-[4-[[[(3-aminophenyl)amino]-carbonyl]amino]benzyl]-2-hydroxyethyl]-N-[(2S)-2-hydroxy-3-phenoxypropyl]carbamate MS (ESI) m/z: 573 (M+Na$^+$)

(2) tert-Butyl N-[(1S)-1-[4-[[[(4-aminophenyl)amino]-carbonyl]amino]benzyl]-2-hydroxyethyl]-N-[(2S)-2-hydroxy-3-phenoxypropyl]carbamate MS (ESI) m/z: 573 (M+Na$^+$)

EXAMPLE 22

To a solution of tert-butyl N-[(1S)-1-[4-[[[(2-aminophenyl)amino]carbonyl]amino]benzyl]-2-hydroxyethyl]-N-[(2S)-2-hydroxy-3-phenoxypropyl]carbamate (20.0 mg) in 1,2-dichloroethane (200 µl) were added successively 1.0 M solution of pyridine in 1,2-dichloroethane (54.5 µl) and 1.0 M solution of methanesulfonyl chloride in 1,2-dichloroethane (43.6 µl) at room temperature. After stirring for 2 hours, the solvent was removed by evaporation and the residue was purified by a recycling preparative high pressure liquid chromatography equipped with a gel permeation chromatography column (eluent: chloroform) to give a light brown solid. The solid was dissolved in 1,2-dichloroethane (200 µl). To the solution was added trifluoroacetic acid (200 µl) and the mixture was stirred for 30 minutes. The solvent was removed by evaporation to give N-[2-[[[[4-[(2S)-3-hydroxy-2-[[(2S)-2-hydroxy-3-phenoxypropyl]amino]propyl]phenyl]amino]-carbonyl]amino]phenyl]methanesulfonamide trifluoroacetate (20.3 mg) as a light brown solid.

MS m/z: 529 (MH$^+$)

EXAMPLE 23

The following compounds were obtained according to a similar manner to that of Example 22.
(1) Methyl N-[2-[[[[4-[(2S)-3-hydroxy-2-[[(2S)-2-hydroxy-3-phenoxypropyl]amino]propyl]phenyl]amino]carbonyl]-amino]phenyl]carbamate trifluoroacetate
MS m/z: 509 (MH$^+$)
(2) N-[3-[[[[4-[(2S)-3-Hydroxy-2-[[(2S)-2-hydroxy-3-phenoxypropyl]amino]propyl]phenyl]amino]carbonyl]-amino]phenyl]methanesulfonamide trifluoroacetate
MS m/z: 529 (MH$^+$)
(3) Methyl N-[3-[[[[4-[(2S)-3-hydroxy-2-[[(2S)-2-hydroxy-3-phenoxypropyl]amino]propyl]phenyl]amino]carbonyl]-amino]phenyl]carbamate trifluroacetate
MS m/z: 509 (MH$^+$)
(4) N-[4-[[[[4-[(2S)-3-Hydroxy-2-[[(2S)-2-hydroxy-3-phenoxypropyl]amino)propyl]phenyl]amino]carbonyl]-amino]phenyl]methanesulfonamide trifluoroacetate
MS m/z: 529 (MH$^+$)
(5) Methyl N-[4-[[[[4-[(2S)-3-hydroxy-2-[[(2S)-2-hydroxy-3-phenoxypropyl]amino]propyl]phenyl]amino]carbonyl]-amino]phenyl]carbamate trifluoroacetate
MS m/z: 509 (MH$^+$)

EXAMPLE 24

To a solution of ethyl 3-[[[[4-[(2S)-2-[N-(tert-butoxycarbonyl)-N-[(2S)-2-hydroxy-3-phenoxypropyl]amino]-3-[(trimethylsilyl)oxy]propyl]phenyl]amino]carbonyl]amino]-benzoate (204 mg) in 1,2-dichloroethane (2.0 ml) was added trifluroacetic acid (2.0 ml) and the solution was stirred at room temperature for 1 hour. The solvent was removed by evaporation and the residue was dissolved in ethyl acetate (10 ml). The solution was washed with aqueous saturated sodium bicarbonate solution (5 ml×1) and brine (10 ml×1) successively, dried over magnesium sulfate, and evaporated to give ethyl 3-[[[[4-[(2S)-3-hydroxy-2-[[(2S)-2-hydroxy-3-phenoxypropyl]amino]propyl]phenyl]amino]carbonyl]amino]-benzoate (148 mg) as a white solid.

EXAMPLE 25

The following compound was obtained according to a similar manner to that of Example 24.
Ethyl 4-[[[[4-[(2S)-3-hydroxy-2-[((2S)-2-hydroxy-3-phenoxypropyl]amino]propyl]phenyl]amino)carbonyl]amino]-benzoate

EXAMPLE 26

To a solution of ethyl 3-[[[[4-[(2S)-3-hydroxy-2-[[(2S)-2-hydroxy-3-phenoxypropyl]amino]propyl]phenyl]-amino]carbonyl]amino]benzoate (148 mg) in ethanol (2.0 ml) was added 1N sodium hydroxide solution (292 µl) and the solution was refluxed for 4 hours. An additional portion of 1N sodium hydroxide solution (58.3 µl) was added and the whole was refluxed for 3 hours. After cooling to room temperature, the solvent was removed by evaporation to give sodium 3-[[[[4-[(2S)-3-hydroxy-2-[[(2S)-2-hydroxy-3-phenoxypropyl]amino]propyl]phenyl]amino]carbonyl]amino)-benzoate (158 mg) as a white solid.
MS m/z: 502 (MH$^+$)

EXAMPLE 27

The following compound was obtained according to a similar manner to that of Example 26.
Sodium 4-[[[[4-[(2S)-3-hydroxy-2-[[(2S)-2-hydroxy-3-phenoxypropyl]amino]propyl]phenyl)amino]carbonyl]amino]-benzoate
MS m/z: 502 (MH$^+$)

EXAMPLE 28

To a solution of sodium 3-[[[[4-[(2S)-3-hydroxy-2-[[(2S)-2-hydroxy-3-phenoxypropyl]amino]propyl]phenyl]-amino]carbonyl]amino]benzoate (50.0 mg) in a mixed solvent of tetrahydrofuran (1.0 ml) and water (1.0 ml) was added 1N sodium hydroxide solution (99.7 µl). To the solution was added di-tert-butyl dicarbonate (27.5 µl) at room temperature and the mixture was stirred for 2 hours. An additional portion of di-tert-butyl dicarbonate (27.5 µl) was added and the mixture was stirred for 30 minutes. To the mixture was added pH 4.0 buffer solution (10 ml) and the resulting suspension was extracted with ethyl acetate (30 ml×1). The organic layer was separated and washed with brine (10 ml×1), dried over magnesium sulfate, and evaporated to give 3-[[[[4-[(2S)-2-[N-(tert-butoxycarbonyl)-N-[(2S)-2-hydroxy-3-phenoxypropyl]amino]-3-hydroxypropyl]phenyl]-amino]carbonyl]amino]benzoic acid (47.3 mg) as a yellow solid.

EXAMPLE 29

The following compound was obtained according to a similar manner to that of Example 28.
4-[[[[4-[(2S)-2-[N-(tert-Butoxycarbonyl)-N-[(2S)-2-hydroxy-3-phenoxypropyl]amino]-3-hydroxypropyl]phenyl]-amino]carbonyl]amino]benzoic acid
MS (negative) m/z: 578 (M–H$^+$)

EXAMPLE 30

To a solution of 3-[[[[4-[(2S)-2-[N-(tert-butoxycarbonyl)-N-[(2S)-2-hydroxy-3-phenoxypropyl]amino]-3-hydroxypropyl]phenyl]amino]carbonyl]amino]benzoic acid (10.0 mg) in N,N-dimethylformamide (100 µl) were added successively a 1.0 M solution of 1-hydroxybenzotriazole hydrate in N,N-dimethylformamide (20.7 µl) and a 1.0 M solution of 1-[3-(dimethylamino)propyl]-3-ethylcarbodiimide in 1,2-dichloroethane (20.7 µl) at room temperature. To the solution was added methylamine hydrochloride (1.4 mg) and the mixture was stirred for 4 hours. The reaction mixture was diluted with ethyl acetate (10 ml) and washed with water (10 ml×1) and brine (10 ml×1) successively, dried over magnesium sulfate, and evaporated to give a pale yellow paste. The crude product was purified by a recycling preparative high pressure liquid chromatography equipped with a gel permeation chromatography column (eluent: chloroform) to give tert-butyl (1S)-2-hydroxy-1-[4-[[[[3-(methylcarbamoyl)phenyl]amino]carbonyl]amino]benzyl]ethyl]-N-[(2S)-2-hydroxy-3-phenoxypropyl]carbamate (7.2 mg) as a pale yellow solid.

EXAMPLE 31

The following compounds were obtained according to a similar manner to that of Example 30.
(1) tert-Butyl N-[(2S)-2-hydroxy-3-phenoxypropyl]-N-[(1S)-2-hydroxy-1-[4-[[[[3-(propylcarbamoyl)phenyl]amino]-carbonyl]amino]benzyl]ethyl]carbamate
(2) tert-Butyl N-[(1S)-1-[4-[[[[3-(dimethylcarbamoyl)-phenyl]amino]carbonyl]amino]benzyl]-2-hydroxyethyl]-N-[(2S)-2-hydroxy-3-phenoxypropyl]carbamate
(3) tert-Butyl N-[(1S)-2-hydroxy-1-[4-[[[[4-(methylcarbamoyl)phenyl]amino]carbonyl]amino]benzyl]-ethyl]-N-[(2S)-2-hydroxy-3-phenoxypropyl]carbamate (4) tert-Butyl N-[(2S)-2-hydroxy-3-phenoxypropyl]-N-[(1S)-2-hydroxy-1-[4-[[[[4-(propylcarbamoyl)phenyl]amino]-carbonyl]amino]benzyl]ethyl]carbamate (5) tert-Butyl N-[(1S)-1-[4-[[[[4-(dimethylcarbamoyl)phenyl]amino]carbonyl]amino]benzyl]-2-hydroxyethyl]-N-[(2S)-2-hydroxy-3-phenoxypropyl]carbamate

EXAMPLE 32

To a solution of tert-butyl N-[(1S)-2-hydroxy-1-[4-[[[3-(methylcarbamoyl)phenyl]amino)carbonyl]amino]benzyl]-ethyl]-N-[(2S)-2-hydroxy-3-phenoxypropyl]carbamate (7.2 mg) in a mixed solvent of 1,2-dichloroethane (100 µl) and methanol (25 µl) was added trifluoroacetic acid (100 µl) and the mixture was stirred at room temperature for 3 hours. The solvent was removed by evaporation to give 3-[[[[4-[(2S)-3-hydroxy-2-[[(2S)-2-hydroxy-3-phenoxypropyl]amino]-propyl]phenyl]amino]carbonyl]amino]-N-methylbenzamide trifluroacetate (7.2 mg) as a pale yellow foam.

MS m/z: 493 (MH$^+$)

EXAMPLE 33

The following compounds were obtained according to a similar manner to that of Example 32.

(1) 3-[[[[4-[(2S)-3-Hydroxy-2-[[(2S)-2-hydroxy-3-phenoxypropyl]amino]propyl]phenyl]amino]carbonyl]-amino]-N-propylbenzamide trifluroacetate MS m/z: 521 (MH$^+$)

(2) 3-[[[[4-[(2S)-3-Hydroxy-2-[[(2S)-2-hydroxy-3-phenoxypropyl]amino]propyl]phenyl]amino]carbonyl]-amino]-N,N-dimethylbenzamide trifluoroacetate MS m/z: 507 (MH$^+$)

(3) 4-[[[[4-[(2S)-3-Hydroxy-2-[[(2S)-2-hydroxy-3-pyhenoxypropyl]amino]propyl]phenyl]amino]carbonyl]-amino]-N-methylbenzamide trifluoroacetate NMR (DMSO-d$_6$, δ): 2.76 (3H, d, J=4.5 Hz), 2.86–4.30 (10H, m), 5.41 (1H, br), 5.83 (1H, br), 6.94–7.00 (3H, m), 7.21 (2H, d, J=8.5 Hz), 7.28–7.36 (2H, m), 7.44 (2H, d, J=8.5 Hz), 7.52 (2H, d, J=8.8 Hz), 7.77 (2H, d, J=8.8 Hz), 8.32 (2H, br), 8.69 (1H, br), 9.11 (1H, br s), 9.31 (1H, br s)

MS m/z: 493 (MH$^+$)

(4) 4-[[[[4-[(2S)-3-Hydroxy-2-[[(2S)-2-hydroxy-3-phenoxypropyl]amino]propyl]phenyl]amino]carbonyl]-amino]-N-propylbenzamide trifluoroacetate NMR (DMSO-d$_6$, δ): 0.88 (3H, t, J=7.4 Hz), 1.43–1.58 (2H, m), 2.80–4.20 (10H, m), 5.44 (1H, br), 5.86 (1H, br), 6.94–7.00 (3H, m), 7.21 (2H, d, J=8.5 Hz), 7.28–7.36 (2H, m), 7.44 (2H, d, J=8.5 Hz), 7.51 (2H, d, J=8.7 Hz), 7.78 (2H, d, J=8.7 Hz), 8.32 (2H, br), 8.92 (1H, br), 9.08 (1H, br s), 9.28 (1H, br s)

MS m/z: 521 (MH$^+$)

(5) 4-[[[[4-[(2S)-3-Hydroxy-2-[[(2S)-2-hydroxy-3-phenoxypropyl]amino]propyl]phenyl]amino]carbonyl]-amino]-N,N-dimethylbenzamide trifluroacetate NMR (DMSO-d$_6$, δ): 2.61–3.65 (7H, m), 2.96 (6H, s), 3.96–4.00 (2H, m), 4.20 (1H, br) 5.32 (1H, br), 5.89 (1H, br), 6.94–7.00 (3H, m), 7.20 (2H, d, J=8.5 Hz), 7.31 (2H, t, J=8.1 Hz), 7.35 (2H, d, J=8.7 Hz), 7.44 (2H, d, J=8.5 Hz), 7.51 (2H, d, J=8.7 Hz), 8.32 (1H, br), 8.67 (1H, br), 8.93 (1H, br s), 9.06 (1H, br s)

MS m/z: 507 (MH$^+$)

EXAMPLE 34

To a solution of N-[4-[(2S)-2-amino-3-hydroxypropyl]phenyl]-N'-phenylurea hydrochloride (222 mg) in ethanol (5.0 ml) were added successively N,N-diisopropylethylamine (264 µl) and (2S)-2-[[4-(benzyloxy)phenoxy)methyl]oxirane (212 mg) and the solution was refluxed for 13.5 hours. After cooling to room temperature, the precipitates were collected by filtration, washed with ethanol, and dried under reduced pressure to give N-[4-[(2S)-2-[[(2S)-3-[4-(benzyloxy)phenoxy]-2-hydroxypropyl]amino]-3-hydroxypropyl]phenyl]-N'-phenylurea (166 mg) as a white solid.

MS m/z: 542 (MH$^+$)

EXAMPLE 35

N-[4-[(2S)-2-[[(2S)-3-[4-(Benzyloxy)phenoxy]-2-hydroxypropyl]amino]-3-hydroxypropyl]phenyl]-N'-phenylurea (159 mg) was dissolved in a mixed solvent of methanol (2.5 ml) and 1,4-dioxane (2.5 ml) under heating. After cooling to room temperature, 10% palladium on activated carbon (50% wet, 159 mg) was added and the mixture was hydrogenated at 1 atm for 4 hours. The catalyst was removed by filtration and washed with methanol. The filtrate was concentrated in vacuo to give N-[4-[(2S)-3-hydroxy-2-[[(2S)-2-hydroxy-3-(4-hydroxyphenoxy)propyl]amino]propyl]phenyl]-N'-phenylurea (129 mg) as a white solid.

IR (KBr): 3456, 3296, 3033, 1643, 1595, 1560, 1511, 1442, 1230, 1101, 1041, 827 cm$^{-1}$

NMR (DMSO-d$_6$, δ): 2.55–2.78 (5H, m), 3.23 (2H, br), 3.73–3.82 (3H, m), 4.52 (1H, br), 4.89 (1H, br), 6.65 (2H, d, J=9.2 Hz), 6.74 (2H, d, J=9.2 Hz), 6.95 (1H, t-like, J=7.3 Hz), 7.09 (2H, d, J=8.4 Hz), 7.25 (2H, d, J=8.3 Hz), 7.34 (2H, d, J=8.4 Hz), 7.44 (2H, d, J=7.6 Hz), 8.57 (1H, br), 8.63 (1H, br), 8.87 (1H, br)

MS m/z: 452 (MH$^+$)

EXAMPLE 36

To a solution of (2S)-3-(4-aminophenyl)-2-[N-benzyl-N-[(2S)-2-hydroxy-3-phenoxypropyl)amino)-1-propanol (300 mg) in 1,2-dichloroethane (3.0 ml) was added N,O-bis(trimethylsilyl)acetamide (182 µl) and the solution was stirred at room temperature for 1 hour. To the solution were added successively 4-(methoxycarbonyl)benzoic acid (160 mg), 1-hydroxybenzotriazole hydrate (120 mg), and 1-[3-(dimethylamino)propyl]-3-ethylcarbodiimide hydrochloride (170 mg) at room temperature. After stirring at the same temperature for 3 hours, N,O-bis(trimethylsilyl)acetamide (182 µl) was added and the mixture was stirred overnight. The mixture was diluted with ethyl acetate (30 ml) and washed with a saturated aqueous sodium bicarbonate solution (30 ml×1), water (30 ml×2) and brine (30 ml×1) successively, dried over magnesium sulfate, and evaporated to give a yellow solid. The solid was dissolved in tetrahydrofuran (3.0 ml). To the solution was added a 1.0 M solution of tetrabutylammonium fluoride in tetrahydrofuran (1.48 ml) at room temperature and the solution was stirred for 10 minutes. The solution was diluted with ethyl acetate (20 ml) and washed with water (20 ml×2) and brine (20 ml×1) successively, dried over magnesium sulfate, and evaporated to give a yellow solid. The crude product was purified by a recycling preparative high pressure liquid chromatography equipped with a gel permeation chromatography column (eluent: chloroform) and silica gel chromatography (eluent: hexane/ethyl acetate=1/1) to give methyl 4-[[[4-[(2S)-2-[N-benzyl-N-[(2S)-2-hydroxy-3-phenoxypropyl]amino]-3-hydroxypropyl]phenyl]amino]carbonyl]benzoate (132 mg) as a pale yellow solid.

MS m/z: 569 (MH$^+$)

EXAMPLE 37

To a solution of methyl 4-[((4-[((2S)-2-(N-benzyl-N-[(2S)-2-hydroxy-3-phenoxypropyl]amino]-3- hydroxypropyl]-phenyl]amino]carbonyl]benzoate (30.0 mg) in methanol (1.0 ml) was added 10% palladium on activated carbon (50% wet, 30 mg) and the mixture was hydrogenated at 1 atm for 2 hours. The catalyst was filtered off and washed with methanol. The filtrate was concentrated in vacuo to give methyl 4-[[[4-[(2S)-3-hydroxy-2-[[(2S)-2-hydroxy-3-phenoxypropyl]amino]-propyl]phenyl]amino]carbonyl]benzoate (21.9 mg) as a white solid.

EXAMPLE 38

To a suspension of methyl 4-[[[4-[(2S)-3-hydroxy-2-[[(2S)-2-hydroxy-3-phenoxypropyl]amino]propyl]phenyl]-amino]carbonyl]benzoate (19.3 mg) in methanol (1.0 ml) was added 1N sodium hydroxide solution (40.3 µl) and the suspension was refluxed for 10 hours. An additional portion of 1N sodium hydroxide solution (40.3 µl) was added and the mixture was refluxed for 3 hours. After cooling to room temperature, the solvent was removed by evaporation to give sodium 4-[[[4-[(2S)-3-hydroxy-2-[[(2S)-2-hydroxy-3-phenoxypropyl]amino]propyl]phenyl]amino]carbonyl]benzoate (20.6 mg) as a white solid.

MS m/z: 487 (MH$^+$)

EXAMPLE 39

To a solution of methyl 4-[[[4-[(2S)-2-[N-benzyl-N-[(2S)-2-hydroxy-3-phenoxypropyl]amino]-3-hydroxypropyl]-phenyl]amino]carbonyl]benzoate (93.6 mg) in methanol (2.0 ml) was added 1N sodium hydroxide solution (329 µl) and the solution was refluxed for 2.5 hours. After cooling to room temperature, the mixture was neutralized by the addition of 1N hydrochloric acid (329 µl). The solvent was removed by evaporation and the residual solid was suspended in water (2.0 ml). The solid was collected by filtration, washed with water, and dried under reduced pressure to give 4-[[[4-[(2S)-2-[N-benzyl-N-[(2S)-2-hydroxy-3-phenoxypropyl]amino]-3-hydroxypropyl]phenyl]amino]carbonyl]benzoic acid (80.2 mg) as a white solid.

MS (negative) m/z: 553 (M−H$^+$)

EXAMPLE 40

To a solution of 4-[[[4-((2S)-2-[N-benzyl-N-[(2S)-2-hydroxy-3-phenoxypropyl]amino]-3-hydroxypropyl]phenyl]-amino]carbonyl]benzoic acid (14.6 mg) in N,N-dimethylformamide (200 µl) were added 1.0 M solution of 1-hydroxybenzotriazole hydrate in N,N-dimethylformamide (31.6 µl) and 1.0 M solution of 1-[3-(dimethylamino)propyl]-3-ethylcarbodiimide in 1,2-dichloroethane (31.6 µl) at room temperature. To the mixture was added methylamine hydrochloride (2.2 mg) and the whole was stirred overnight. The reaction mixture was diluted with ethyl acetate (10 ml) and washed with water (10 ml×1) and brine (10 ml×1) successively, dried over magnesium sulfate, and evaporated to give a pale yellow paste. The crude product was purified by a recycling preparative high pressure liquid chromatography equipped with a gel permeation chromatography column (eluent: chloroform) to give N$^1$-[4-[(2S)-2-[N-benzyl-N-[(2S)-2-hydroxy-3-phenoxypropyl]amino]-3-hydroxypropyl]-phenyl]-N$^4$-methylterephthalamide (14.0 mg) as a white solid.

EXAMPLE 41

The following compounds were obtained according to a similar manner to that of Example 40.
(1) N$^1$-[4-[(2S)-2-[N-Benzyl-N-[(2S)-2-hydroxy-3-phenoxypropyl]amino]-3-hydroxypropyl]phenyl]-N$^4$,N$^4$-dimethylterephthalamide
(2) N$^1$-[4-[(2S)-2-[N-Benzyl-N-[(2S)-2-hydroxy-3-phenoxypropyl]amino]-3-hydroxypropyl]phenyl]-N$^4$-propylterephthalamide

EXAMPLE 42

To a solution of N$^1$-[4-[(2S)-2-[N-benzyl-N-[(2S)-2-hydroxy-3-phenoxypropyl]amino]-3-hydroxypropyl]phenyl]-N$^4$-methylterephthalamide (14.0 mg) in methanol (0.5 ml) was added 10% palladium on activated carbon (50% wet, 14.0 mg) and the mixture was hydrogenated at 1 atm for 3 hours. The catalyst was filtered off and washed with methanol. The filtrate was concentrated in vacuo to give N$^1$-[4-[(2S)-3-hydroxy-2-[[(2S)-2-hydroxy-3-phenoxypropyl]amino]propyl]-phenyl]-N$^4$-methylterephthalamide (9.7 mg) as a white solid.

MS m/z: 478 (MH$^+$)

EXAMPLE 43

The following compounds were obtained according to a similar manner to that of Example 42.
(1) N$^1$-[4-[(2S)-3-Hydroxy-2-[[(2S)-2-hydroxy-3-phenoxypropyl]amino]propyl]phenyl]-N$^4$,N$^4$-dimethylterephthalamide
MS m/z: 492 (MH$^+$)
(2) N$^1$-[4-[(2S)-3-Hydroxy-2-[[(2S)-2-hydroxy-3-phenoxypropyl]amino]propyl]phenyl]-N$^4$-propylterephthalamide
MS m/z: 505 (MH$^+$)

EXAMPLE 44

To a solution of tert-butyl N-[(1S)-1-(4-aminobenzyl)-2-hydroxyethyl]-N-[(2S)-2-hydroxy-3-phenoxypropyl]carbamate (200 mg) in N,N-dimethylformamide (2.0 ml) was added successively 1-methyl-1H-pyrrole-2-caroxylic acid (72.1 mg) and 1-hydroxybenzotriazole hydrate (77.9 mg). To the mixture was added 1-[3-(dimethylamino)propyl]-3-ethylcarbodiimide hydrochloride (110 mg) at room temperature and the mixture was stirred overnight. The mixture was diluted with ethyl acetate (20 ml) and washed with water (20 ml×2), a saturated aqueous sodium hydrogencarbonate solution (20 ml×1) and brine (20 ml×1) successively. The organic solution was dried over magnesium sulfate, filtered, and evaporated to give a yellow solid. The crude product was purified by a recycling preparative high pressure liquid chromatography equipped with a gel permeation chromatography column (eluent: chloroform) to give tert-butyl N-[(1S)-2-hydroxy-1-[4-[[(1-methyl-1H-pyrrol-2-yl)carbonyl]amino]benzyl]ethyl]-N-[(2S)-2-hydroxy-3-phenoxypropyl]carbamate (163 mg) as a white foam.

MS (ESI) m/z: 546 (M+Na$^+$)

EXAMPLE 45

The following compounds were obtained according to a similar manner to that of Example 44.
(1) tert-Butyl N-[(2S)-2-hydroxy-3-phenoxypropyl]-N-[(1S)-2-hydroxy-1-[4-[[(2-phenoxy-3-pyridyl)carbonyl]amino]-benzyl]ethyl]carbamate
MS m/z: 636 (M+Na$^+$)
(2) tert-Butyl N-[(2S)-2-hydroxy-3-phenoxypropyl]-N-[(1S)-2-hydroxy-1-[4-[(8-quinolinylcarbonyl)amino]benzyl]-ethyl]carbamate
MS m/z: 594 (M+Na$^+$)
(3) tert-Butyl N-[(2S)-2-hydroxy-3-phenoxypropyl]-N-[(1S)-2-hydroxy-1-[4-[[[5-[4-(trifluoromethyl)phenyl]-1,3-oxazol-4-yl]carbonyl]amino]benzyl]ethyl]carbamate
MS m/z: 678 (M+Na$^+$)

(4) tert-Butyl N-[(1S)-2-hydroxy-1-[4-[[(5-methyl-1-phenyl-1H-pyrazol-4-yl)carbonyl]amino]benzyl]ethyl]-N-[(2S)-2-hydroxy-3-phenoxypropyl]carbamate
MS m/z: 623 (M+Na$^+$)

(5) tert-Butyl N-[(1S)-2-hydroxy-1-[4-[[(2-methyl-1H-benzimidazol-5-yl)carbonyl]amino]benzyl]ethyl]-N-[(2S)-2-hydroxy-3-phenoxypropyl)carbamate
MS m/z: 597 (M+Na$^+$)

(6) tert-Butyl N-[(1S)-2-hydroxy-1-[4-[(1H-indol-5-ylcarbonyl)amino]benzyl]ethyl]-N-[(2S)-2-hydroxy-3-phenoxypropyl]carbamate
MS m/z: 582 (M+Na$^+$)

(7) tert-Butyl N-[(1S)-2-hydroxy-1-[4-[[(1-methyl-1H-indol-3-yl)carbonyl]amino]benzyl]ethyl]-N-[(2S)-2-hydroxy-3-phenoxypropyl]carbamate
MS m/z: 596 (M+Na$^+$)

(8) tert-Butyl N-[(2S)-2-hydroxy-3-phenoxypropyl]-N-[(1S)-2-hydroxy-1-[4-[(1H-pyrrol-3-ylcarbonyl)amino]-benzyl]ethyl]carbamate
MS m/z: 532 (M+Na$^+$)

(9) tert-Butyl N-[(2S)-2-hydroxy-3-phenoxypropyl]-N-[(1S)-2-hydroxy-1-[4-[(1H-pyrrol-2-ylcarbonyl)amino]benzyl]-ethyl]carbamate
NMR (CDCl$_3$, δ): 1.46 (9H, s), 2.35–4.45 (10H, m), 6.21–6.36 (1H, m), 6.60–7.35 (9H, m), 7.51 (2H, d, J=8 Hz), 7.58 (1H, br s), 9.59 (1H, br s)
MS m/z: 532 (M$^+$+Na)

EXAMPLE 46 tert-Butyl N-[(1S)-2-hydroxy-1-[4-[[(1-methyl-1H-pyrrol-2-yl)carbonyl]amino]benzyl]ethyl]-N-[(2S)-2-hydroxy-3-phenoxypropyl]carbamate (158 mg) was dissolved in 4N hydrogen chloride in ethanol (2.0 ml) and the solution was stirred at room temperature for 2 hours. The solvent was removed by evaporation and the residual solid was dried under reduced pressure to give N-[4-[(2S)-3-hydroxy-2-[[(2S)-2-hydroxy-3-phenoxypropyl]amino]propyl]phenyl]-1-methyl-1H-pyrrole-2-carboxamide hydrochloride (125 mg) as a pale orange crystalline solid.
MS m/z: 424 (M+Na$^+$)

EXAMPLE 47

The following compounds were obtained according to a similar manner to that of Example 46.
(1) N-[4-[(2S)-3-Hydroxy-2-[[(2S)-2-hydroxy-3-phenoxypropyl]amino]propyl]phenyl]-2-phenoxynicotinamide hydrochloride
MS m/z: 514 (MH$^+$)

(2) N-[4-[(2S)-3-Hydroxy-2-[[(2S)-2-hydroxy-3-phenoxypropyl]amino]propyl]phenyl]-8-quinolinecarboxamide dihydrochloride
MS m/z: 472 (MH$^+$)

(3) N-[4-[(2S)-3-Hydroxy-2-[[(2S)-2-hydroxy-3-phenoxypropyl]amino]propyl]phenyl]-5-[4-(trifluoromethyl)phenyl]-1,3-oxazole-4-carboxamide hydrochloride
MS m/z: 556 (M+Na$^+$)

(4) N-[4-[(2S)-3-Hydroxy-2-[[(2S)-2-hydroxy-3-phenoxypropyl]amino]propyl]phenyl]-5-methyl-1-phenyl-1H-pyrazole-4-carboxamide hydrochloride
MS m/z: 501 (M+Na$^+$)

(5) N-[4-[(2S)-3-Hydroxy-2-[[(2S)-2-hydroxy-3-phenoxypropyl]amino]propyl]phenyl]-2-methyl-1H-benzimidazole-5-carboxamide dihydrochloride
MS m/z: 475 (MH$^+$)

(6) N-[4-[(2S)-3-Hydroxy-2-[[(2S)-2-hydroxy-3-phenoxypropyl]amino]propyl]phenyl]-1H-indole-5-carboxamide hydrochloride
MS m/z: 460 (M+Na$^+$)

(7) N-[(4-[(2S)-3-Hydroxy-2-[[(2S)-2-hydroxy-3-phenoxypropyl]amino]propyl]phenyl]-1-methyl-1H-indole-3-carboxamide hydrochloride
MS m/z: 474 (MH$^+$)

EXAMPLE 48

To a solution of tert-butyl N-[(1S)-1-(4-aminobenzyl)-2-hydroxyethyl]-N-[(2R)-2-(3-chlorophenyl)-2-hydroxyethyl]carbamate (120 mg) in N,N-dimethylformamide (2.0 ml) was added successively 4-phenyl-1H-pyrrole-3-carboxylic acid (64.0 mg) and 1-hydroxybenzotriazole hydrate (46.2 mg). To the mixture was added 1-[3-(dimethylamino)propyl]-3-ethylcarbodiimide hydrochloride (65.6 mg) at room temperature and the mixture was stirred overnight. The mixture was diluted with ethyl acetate (20 ml) and washed with water (20 ml×2), a saturated aqueous sodium hydrogencarbonate solution (20 ml×1) and brine (20 ml×1) successively. The organic solution was dried over magnesium sulfate, filtered, and evaporated to give a yellow solid. The crude product was purified by a recycling preparative high pressure liquid chromatography equipped with a gel permeation chromatography column (eluent: chloroform) to give tert-butyl N-[(2R)-2-(3-chlorophenyl)-2-hydroxyethyl]-N-[(1S)-2-hydroxy-1-[4-[[(4-phenyl-1H-pyrrol-3-yl)carbonyl]amino]benzyl]ethyl]carbamate (16 mg) as a yellow foam.
MS (ESI) m/z: 612 (M+Na$^+$)

EXAMPLE 49

The following compounds were obtained according to a similar manner to that of Example 48.
(1) tert-Butyl N-[(2R)-2-(3-chlorophenyl)-2-hydroxyethyl]-N-[(1S)-2-hydroxy-1-[4-[[(1-methyl-1H-indol-5-yl)carbonyl]amino]benzyl]ethyl]carbamate
MS (ESI) m/z: 600 (M+Na$^+$)

(2) Methyl 4-[[[4-[(2S)-2-[N-(tert-butoxycarbonyl)-N-[(2R)-2-(3-chlorophenyl)-2-hydroxyethyl]amino]-3-hydroxypropyl]phenyl]amino]carbonyl]benzoate
MS m/z: 483 and 485 (MH$^+$–100)

EXAMPLE 50 tert-Butyl N-[(2R)-2-(3-chlorophenyl)-2-hydroxyethyl]-N-[(1S)-2-hydroxy-1-[4-[[(4-phenyl-1H-pyrrol-3-yl)carbonyl]amino]benzyl]ethyl]carbamate (13.3 mg) was dissolved in 4N hydrogen chloride in ethanol (0.5 ml) and the solution was stirred at room temperature for 5 hours. The solvent was removed by evaporation to give N-[4-(2S)-2-[[(2R)-2-(3-chlorophenyl)-2-hydroxyethyl]amino]-3-hydroxypropyl]phenyl]-4-phenyl-1H-pyrrole-3-carboxyamide hydrochloride (12.8 mg) as a pale yellow solid.
MS m/z: 490 (MH$^+$)

EXAMPLE 51

The following compounds were obtained according to a similar manner to that of Example 50.
(1) Methyl 4-[[[4-[(2S)-2-[[(2R)-2-(3-chlorophenyl)-2-hydroxyethyl]amino]-3-hydroxypropyl]phenyl]amino]-carbonyl]benzoate hydrochloride
MS m/z: 483 (MH$^+$)

(2) N-[4-[(2S)-3-Hydroxy-2-[[[(2S)-2-hydroxy-3-phenoxypropyl]amino]propyl]phenyl]-1H-pyrrole-2-carboxamide hydrochloride
NMR (DMSO-d$_6$, δ) 2.70–3.75 (7H, m), 3.84–4.12 (2H, m), 4.12–4.40 (1H, m), 5.41 (1H, m), 5.89 (1H, m), 6.16 (1H, m), 6.80–7.12 (5H, m), 7.12–7.44 (4H, m), 7.72 (2H, d, J=8 Hz), 8.42 (1H, br s), 8.93 (1H, br s), 9.81 (1H, br s), 11.70 (1H, br s)

MS m/z: 410 (M$^+$+1)

EXAMPLE 52 tert-Butyl N-[(2R)-2-(3-chlorophenyl)-2-hydroxyethyl]-N-[(1S)-2-hydroxy-1-(4-[[(1-methyl-1H-indol-5-yl)carbonyl]amino]benzyl]ethyl]carbamate (101 mg) was dissolved in 4N hydrogen chloride in ethanol (1.0 ml) and the solution was stirred at room temperature for 5 hours. The solvent was removed by evaporation and the residual solid was dissolved in methanol. To the solution was added 1N sodium hydroxide solution (175 μl) and the solvent was removed by evaporation. The residue was chromatographed on silica gel (eluent: chloroform/methanol=9/1) to give N-[4-[(2S)-2-[[(2R)-2-(3-chlorophenyl)-2-hydroxyethyl]amino]-3-hydroxypropyl]phenyl]-1-methyl-1H-indole-5-carboxamide (34.2 mg) as a pale yellow solid.

MS m/z: 478 (MH$^+$)

EXAMPLE 53

To a suspension of methyl 4-[[[4-[(2S)-2-[[(2R)-2-(3-chlorophenyl)-2-hydroxyethyl]amino]-3-hydroxypropyl]phenyl]amino]carbonyl]benzoate hydrochloride (101 mg) in methanol (4.0 ml) was added 1N sodium hydroxide solution (486 μl) and the mixture was refluxed for 90 minutes. After cooling to room temperature, the solvent was removed by evaporation. The residual solid was applied on a solid phase extraction cartridge (BOND ELUT C18, 20 ml, VARIAN) and eluted with water and methanol successively. The eluents containing the target compound were combined and concentrated in vacuo to give sodium 4-[[[4-[(2S)-2-[[(2R)-2-(3-chlorophenyl)-2-hydroxyethyl]amino]-3-hydroxypropyl]-phenyl]amino]carbonyl]benzoate (66.7 mg) as an off-white solid.

MS m/z: 491 (MH$^+$)

EXAMPLE 54

To a stirred suspension of (2S)-3-(4-aminophenyl)-2-[N-benzyl-N-[(2S)-3-[4-(benzyloxy)phenoxy]-2-hydroxypropyl]amino]-1-propanol (51.3 mg), 1H-pyrrole-2-carboxylic acid (11.9 mg) and 1-hydroxybenzotriazole hydrate (13.5 mg) in 1,2-dichloromethane (1.0 ml) was added 1-[3-(dimethylamino)propyl]-3-ethylcarbodiimide hydrochloride (21.5 mg) under ice-cooling and the resulting mixture was stirred at room temperature overnight. The mixture was diluted with saturated aqueous sodium hydrogencarbonate solution and extracted twice with ethyl acetate. The extracts were combined, washed twice with brine, dried over magnesium sulfate, and concentrated in vacuo. The residue was purified by preparative thin layer chromatography (eluent: toluen/ethyl acetate=5/5) to give N-[4-[(2S)-2-[N-benzyl-N-[(2S)-3-[4-(benzyloxy)phenoxy]-2-hydroxypropyl]-amino]-3-hydroxypropyl]phenyl]-1H-pyrrole-2-carboxamide (43 mg) as a gum.

MS m/z: 606 (MH$^+$)

EXAMPLE 55

To a solution of N-[4-[(2S)-2-[N-benzyl-N-[(2S)-3-[4-(benzyloxy)phenoxy]-2-hydroxypropyl]amino]-3-hydroxypropyl]-phenyl]-1H-pyrrole-2-carboxamide (40 mg) in methanol (2.0 ml) was added 10% palladium on activated carbon (50% wet, 10 mg) and the mixture was hydrogenated at 1 atm for 3 hours. The catalyst was filtered off and washed with methanol. The filtrate was concentrated in vacuo and the residue was powdered from ether and dried to give N-[4-[(2S)-3-hydroxy-2-[[(2S)-2-hydroxy-3-(4-hydroxyphenoxy)propyl]amino]propyl]-phenyl]-1H-pyrrole-2-carboxamide (26 mg) as a gray powder.

MS m/z: 426 (MH$^+$)

EXAMPLE 56

Under nitrogen, a solution of (S)-N-[4-(2-amino-3-hydroxypropyl)phenyl]benzamide (60 mg) and (S)-4-(2-oxiranylmethoxy)carbazole (42.5 mg) in ethanol (10 ml) was refluxed for 18 hours. The mixture was evaporated in vacuo. The residue was purified by column chromatography on silica gel (chloroform:methanol=100:1) to give N-[4-[((2S)-2-[[(2S)-3-(9H-carbazol-4-yloxy)-2-hydroxypropyl]amino]-3-hydroxypropyl]phenyl]benzamide (50 mg) as a colorless foam.

IR (KBr): 3300–3000, 1725, 1650, 1602, 1511, 1446, 1259 cm$^{-1}$

NMR (MeOD-d$_4$, δ): 2.50–3.10 (4H, m), 3.20–3.70 (3H, m), 4.10–4.00 (3H, m), 6.60 (1H, d, J=7.8 Hz), 7.05–8.00 (14H, m), 8.3 (1H, d, J=7.8 Hz)

MS m/z: 510 (M+1)

EXAMPLE 57

The following compounds were obtained according to a similar manner to that of Example 56.

(1) N-[4-[(2S)-2-[[(2R)-2-(3-Chlorophenyl)-2-hydroxyethyl]amino]-3-hydroxypropyl]phenyl]benzamide IR (KBr): 3500–3000, 1650, 1598, 1515, 1411, 1321, 1263 cm$^{-1}$ NMR (MeOD-d$_4$, δ): 2.70–3.20 (4H, m), 3.40–3.80 (3H, m), 4.70–4.80 (1H, m), 7.10–7.70 (11H, m), 7.90–8.00 (2H, m)

MS m/z: 425 (M+1)

(2) N-[4-[(2S)-2-[[(2S)-3-(1H-Indoly-4-yloxy)-2-hydroxypropyl]amino]1–3-hydroxypropyl]phenyl]benzamide IR (KBr): 3400–3000, 1658, 1646, 1598, 1513, 1444, 1241, 1091 cm$^{-1}$ NMR (MeOD-d$_4$, δ): 2.70–3.20 (5H, m), 3.30–3.70 (2H, m), 4.00–4.25 (3H, m), 6.40–6.60 (2H, m), 6.90–8.00 (12H, m)

MS m/z: 460 (M+1)

EXAMPLE 58

In 4N hydrogen chloride in ethanol (2.0 ml), tert-butyl N-[(2S)-2-hydroxy-3-phenoxypropyl]-N-[(1S)-2-hydroxy-1-[4-[(1H-pyrrol-3-ylcarbonyl)amino]benzyl]ethyl] carbamate (113.5 mg) was dissolved and the solution was stirred at room temperature for 30 hours. After concentration under reduced pressure, the residue was extracted with ethyl acetate (20 ml) and washed with saturated sodium hydrogencarbonate aqueous solution (20 ml). The organic layer was separated and the aqueous layer was extracted twice with ethyl acetate (20 ml). The organic layers were combined and washed with brine, and dried over magnesium sulfate to give N-[4-[(2S)-3-hydroxy-2-[[(2S)-2-hydroxy-3-phenoxypropyl]amino]propyl]-phenyl]-1H-pyrrole-3-carboxamide (18.2 mg) as a yellow solid.

MS m/z: 410 (MH$^+$), 432 (M+Na$^+$)

EXAMPLE 59
Step 1: Preparation of Polymer-Bound HOBt ester (1)

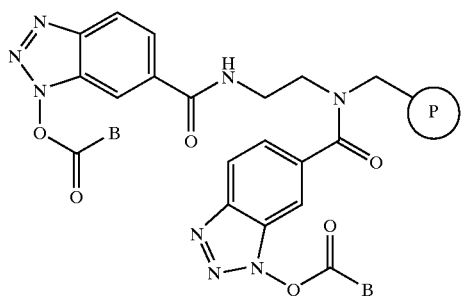

1

Polystyrene-bound 1-hydroxybenzotriazole (HOBt), bis-(6-carboxy-HOBt)-N-(2-aminoethyl)aminomethyl polystyrene (200 mg, 1.54 mmole/g, Novabiochem) was added to a 6 ml polypropylene tube (Varian). A solution of a carboxylic acid derivative

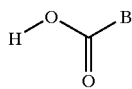

or hydrochloride thereof corresponding to an objective amide derivative in N,N-dimethylformamide (DMF) (0.4 M, 2.3 ml) was added to the tube and shaken for 5 minutes. To the reaction mixture was added 1,3-diisopropylcarbodiimide (72.4 μl) and shaken for 3 hours at ambient temperature. The resin was filtered and washed well with DMF. An additional 2.3 ml of 0.4 M carboxylic acid derivative solution in DMF and 1,3-diisopropylcarbodiimide (72.4 μl) were added and shaken for 3 hours at ambient temperature. The resultant resin was filtered, washed well subsequently with DMF, dichloromethane (DCM), diethyl ether, and dried under reduced pressure to give polymer-bound HOBt ester (1).

Step 2: General Procedure for the Amide Derivatives (2)

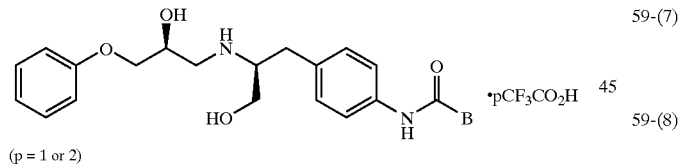

2

(p = 1 or 2)

To a 6 ml polypropylene tube (Varian) was added 0.024 M solution of tert-butyl N-[(1S)-1-(4-aminobenzyl)-2-hydroxyethyl]-N-[(2S)-2-hydroxy-3-phenoxypropyl] carbamate in DCM (1 ml) and N,O-bis(trimethylsilyl)acetamide (18 μl). After shaking for 30 minutes, polymer-bound HOBt ester (100 mg) was added to the reaction mixture and shaken overnight at ambient temperature. The polymer was filtered, washed well with DCM and concentrated under reduced pressure. To the resultant residue was added 1 ml of 50% trifluoroacetic acid (TFA) in DCM and shaken for 3 hours at ambient temperature. The solvent was evaporated and purified by HPLC (reverse phase $C_{18}$, 0–80% 0.1% TFA in acetonitrile/0.1% TFA in water. The fractions containing the desired compound were combined, evaporated and dried under reduced pressure to give the objective amide derivative (2).

Following the Steps 1 and 2 outlined above, the compounds listed in Table 1 were obtained.

TABLE 1

B structure with ·pCF$_3$CO$_2$H (p = 1 or 2)

| Example | B | p | MS [M + H]$^+$ Data |
|---|---|---|---|
| 59-(1) | 2-chlorophenyl | 1 | 455 |
| 59-(2) | 2-furyl | 1 | 411 |
| 59-(3) | 2-(1-propenyl)furan | 1 | 437 |
| 59-(4) | 2,4-dimethoxyphenyl | 1 | 481 |
| 59-(5) | 3-furyl | 1 | 411 |
| 59-(6) | 2-thienyl | 1 | 427 |
| 59-(7) | 3-thienyl | 1 | 427 |
| 59-(8) | 2-indolyl | 1 | 460 |
| 59-(9) | 2-benzothienyl | 1 | 477 |
| 59-(10) | 4-pyridylethyl | 2 | 450 |
| 59-(11) | quinoxalinyl | 2 | 473 |

TABLE 1-continued

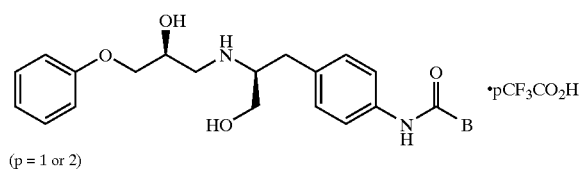

•pCF₃CO₂H (p = 1 or 2)

| Example | B | p | MS [M + H]⁺ Data |
|---|---|---|---|
| 59-(12) | (2-methoxyphenyl, methyl) | 1 | 451 |
| 59-(13) | (methyl-tetrahydronaphthyl) | 1 | 475 |

EXAMPLE 60
General Procedure for the Amide Derivatives (3)

(p = 1 or 2)

To a solution of tert-butyl N-[(1S)-1-(4-aminobenzyl)-2-[(trimethylsilyl)oxy]ethyl]-N-[(2S)-3-phenoxy-2-[(trimethylsilyl)oxy]propyl]carbamate in N,N-dimethylformamide (DMF) (0.059 M, 300 µl) was added a carboxylic acid derivative

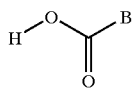

or hydrochloride thereof corresponding to an objective amide derivative (21.4 µM) and a solution of benzotriazol-1-yloxytripyrrolidinophosphonium hexafluorophosphate in DMF (0.142 M, 150 µl). After shaking for 5 minutes, to the reaction mixture was added N,N-diisopropylethylamine (DIEA, 7.8 µl) and shaken overnight at ambient temperature. In the case that 3-pyridylacetic acid was used as a carboxylic acid derivative, additional 15.6 µl of DIEA was added to the reaction mixture. The reaction mixture was loaded onto the solid-phase extraction cartridge (Waters, Oasis) conditioned using acetonitrile (CH₃CN, 6 ml) and water (6 ml), washed with water (6 ml) and 10% CH₃CN in water (6 ml), and eluted with CH₃CN (6 ml). Evaporation of the solvent gave a residue, to which was added 50% trifluoroacetic acid in dichloromethane (DCM) (1 ml) and shaken for 3 hours at ambient temperature. Evaporation of the solvent gave a residue, which was purified by HPLC (reverse phase C₁₈, 0–80% 0.1% TFA in CH₃CN/0.1% TFA in water). The fractions containing the desired compound were combined, evaporated and dried under reduced pressure to give the objective amide derivative (3).

Following the procedure outlined above, the compounds listed in Table 2 were obtained.

TABLE 2

(structure shown)

•pCF₃CO₂H (p = 1 or 2)

| Example | B | p | MS [M + H]⁺ Data |
|---|---|---|---|
| 60-(1) | 2-methylpyridyl | 1 | 422 |
| 60-(2) | 3-ethylindolyl | 1 | 474 |
| 60-(3) | methylcyclohexyl | 1 | 427 |
| 60-(4) | 2,4-difluoromethylphenyl | 1 | 457 |
| 60-(5) | 3-ethylpyridyl | 2 | 436 |
| 60-(6) | 4-methylpyridyl | 2 | 422 |
| 60-(7) | 4-methylquinolyl | 1 | 472 |
| 60-(8) | 1-methylisoquinolyl | 1 | 472 |
| 60-(9) | 4-methylimidazolyl | 2 | 411 |

TABLE 2-continued

Structure (shown at top of both columns):

OH, phenoxy-CH2-CH(OH)-CH2-NH-CH(CH2OH)-CH2-C6H4-NH-C(=O)-B · pCF3CO2H (p = 1 or 2)

| Example | B | p | MS [M + H]+ Data |
|---|---|---|---|
| 60-(10) | 6-methyl-1H-indol-3-yl | 1 | 460 |
| 60-(11) | 3-methyl-1H-indazol-... | 1 | 461 |
| 60-(12) | 4-methyl-3-phenyl-1H-pyrrol-... | 1 | 486 |
| 60-(13) | 2-ethyl-1H-benzimidazol-... | 1 | 475 |
| 60-(14) | 1,5-dimethyl-1H-indol-... | 1 | 474 |
| 60-(15) | 2-methylphenyl | 1 | 435 |
| 60-(16) | 3-methylphenyl | 1 | 435 |
| 60-(17) | 4-methylphenyl | 1 | 435 |
| 60-(18) | 2-fluoro-methylphenyl | 1 | 439 |
| 60-(19) | 3-fluoro-methylphenyl | 1 | 439 |
| 60-(20) | 4-fluoro-methylphenyl | 1 | 439 |
| 60-(21) | 2-nitro-methylphenyl | 1 | 466 |
| 60-(22) | 3-nitro-methylphenyl | 1 | 466 |
| 60-(23) | 4-nitro-methylphenyl | 1 | 466 |
| 60-(24) | 2-CF3-methylphenyl | 1 | 489 |
| 60-(25) | 3-CF3-methylphenyl | 1 | 489 |
| 60-(26) | 4-CF3-methylphenyl | 1 | 489 |

EXAMPLE 61
General Procedure for the Amide Derivatives (4)

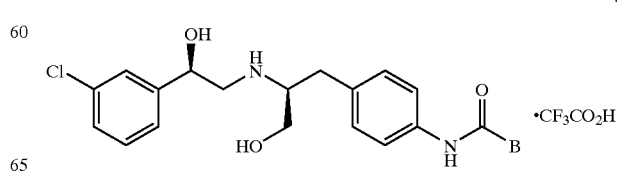

(4)

·CF3CO2H

Method A

To a solution of a carboxylic acid derivative

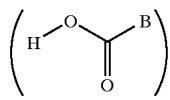

corresponding to an objective amide derivative (0.024 mmol) in NMP (36 μl) was added 1.0 M solution of N,O-bis(trimethylsilyl)acetamide (BSA) in N-methyl-2-pyrrolidinone (NMP) (12 μl, 0.012 mmol). After shaking for 30 minutes at room temperature, 1.0 M solution of N,N-diisopropylethylamine (DIEA) in NMP (50 μl, 0.05 mmol) and 0.5 M solution of benzotriazol-1-yloxytripyrrolidino-phosphonium hexafluorophosphate in NMP (60 μl, 0.03 mmol) were added to the solution and the mixture was shaken for 30 minutes at room temperature. In another vessel, a solution of tert-butyl N-[(1S)-1-(4-aminobenzyl)-2-hydroxyethyl]-N-[(2R)-2-(3-chlorophenyl)-2-hydroxyethyl]carbamate (0.02 mmol) in NMP (20 μl) and 1.0 M solution of BSA in NMP (20 μl, 0.02 mmol) was shaken for 30 minutes at room temperature, and the solution was added to the above activated ester solution. The mixture was allowed to warm to 50° C. and shaken for 2 hours. After cooling to room temperature, 0.5 ml of 95% trifluoroacetic acid (TFA) in water was added to the solution and shaken for 15 hours. The mixture was concentrated under reduced pressure and purified by HPLC (reverse phase $C_{18}$, 0–80% 0.1% TFA in acetonitrile ($CH_3CN$)/0.1% TFA in water. The fractions containing the desired compound were combined, concentrated and dried under reduced pressure to give the objective amide derivative (4).

Method B

To a solution of a carboxylic acid derivative

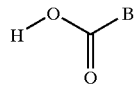

or hydrochloride thereof corresponding to an objective amide derivative (0.024 mmol) in NMP (36 μl) was added 1.0 M solution of BSA in NMP (12 1, 0.012 mmol). After shaking for 30 minutes at room temperature, 0.5 M solution of 1-hydroxybenzotriazole (HOBt) in NMP (60 μl, 0.03 mmol) and 0.5 M solution of 1-ethyl 3-(3'-dimethylaminopropyl)carbodiimide (EDC) in NMP (60 μl, 0.03 mmol) were added to the solution and the mixture was shaken for 30 minutes at room temperature. In another vessel, a solution of tert-butyl N-[(1S)-1-(4-aminobenzyl)-2-hydroxyethyl]-N-[(2R)-2-(3-chlorophenyl)-2-hydroxyethyl]carbamate (0.02 mmol) in NMP (20 μl) and 1.0 M solution of BSA in NMP (20 μl, 0.02 mmol) was shaken for 30 minutes at room temperature, and the solution was added to the above activated ester solution. The mixture was allowed to warm to 50° C. and shaken for 15 hours. After cooling to room temperature, 0.5 ml of 95% TFA in water was added to the solution and shaken for 15 hours. The mixture was concentrated under reduced pressure and purified by HPLC (reverse phase $C_{18}$, 0–80% 0.1%, TFA in $CH_3CN$/0.1% TFA in water). The fractions containing the desired compound were combined, concentrated and dried under reduced pressure to give the objective amide derivative (4).

Following Method A or Method B outlined above, the compounds listed in Table 3 were obtained.

TABLE 3

[Structure shown: 3-chlorophenyl-CH(OH)-CH2-NH-CH(CH2-4-aminophenyl-NHC(O)-B)-CH2OH · $CF_3CO_2H$]

| Example | B | MS [M + H]$^+$ Data | Method |
|---|---|---|---|
| 61-(1) | 4-methylpyridinyl | 426, 428 | A |
| 61-(2) | methylpyrazinyl | 427, 429 | A |
| 61-(3) | methylthienyl | 431, 433 | A |
| 61-(4) | methylfuryl | 415, 416 | A |
| 61-(5) | methylnaphthyl | 475 | A |
| 61-(6) | methylquinolinyl | 476, 477 | A |
| 61-(7) | methylquinolinyl | 476, 477 | A |
| 61-(8) | methylquinolinyl | 476 | A |
| 61-(9) | methylquinolinyl | 476, 477 | A |
| 61-(10) | methylquinoxalinyl | 477, 478 | A |

TABLE 3-continued

Structure (shared): 3-chlorophenyl-CH(OH)-CH2-NH-CH(CH2OH)-CH2-C6H4-NH-C(=O)-B · CF3CO2H

| Example | B | MS [M + H]+ Data | Method |
|---|---|---|---|
| 61-(11) | 4-(3-methylphenyl)-2-phenylthiazol-... | 585, 586 | A |
| 61-(12) | 1-methyl-1H-pyrrol-2-yl (with CH3) | 428 | A |
| 61-(13) | 3-methyl-2-phenoxypyridin-... | 518 | A |
| 61-(14) | 2-methoxyphenyl (methyl) | 455 | A |
| 61-(15) | 3-methoxyphenyl (methyl) | 455 | A |
| 61-(16) | 4-methoxyphenyl (methyl) | 455, 456 | A |
| 61-(17) | 2-methylpyridin-... | 426 | A |
| 61-(18) | 3-methylpyridin-... | 426 | A |
| 61-(19) | 3-methylthiophen-... | 431 | A |
| 61-(20) | 3-methylfuran-... | 415 | A |
| 61-(21) | 4-(3-methylphenyl)-2-methylthiazol-... | 522, 523 | A |
| 61-(22) | 4-methylquinolin-... | 476, 478 | A |
| 61-(23) | 1-methylisoquinolin-... | 476 | A |
| 61-(24) | 6-methylnaphthalen-... | 475, 476 | A |
| 61-(25) | 3-methylisoquinolin-... | 476, 477 | A |
| 61-(26) | 3-methylquinoxalin-... | 478 | A |
| 61-(27) | 2-methyl-4-methoxyquinolin-... | 506 | A |

TABLE 3-continued

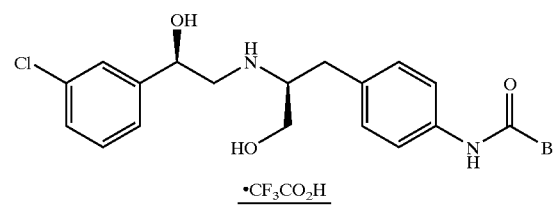
•CF$_3$CO$_2$H

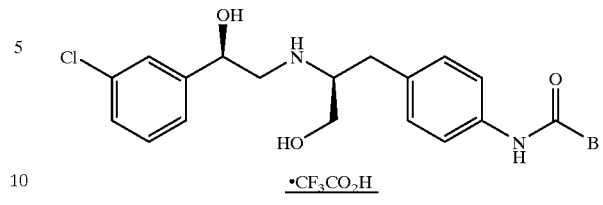
•CF$_3$CO$_2$H

| Example | B | MS [M + H]$^+$ Data | Method |
|---|---|---|---|
| 61-(28) | 2-methylbenzofuran-7-OCH$_3$ | 495 | A |
| 61-(29) | 2-methyl-3-chlorophenyl | 459, 461 | A |
| 61-(30) | 3-chloro-methylphenyl | 459, 461 | A |
| 61-(31) | 4-chloro-methylphenyl | 459 | A |
| 61-(32) | 3-methyl-1H-indole | 478, 479 | A |
| 61-(33) | 2-methyl-1H-pyrrole | 414 | B |
| 61-(34) | 6-methyl-1H-indole | 464 | B |
| 61-(35) | 5-methyl-1H-indole | 464, 465 | B |
| 61-(36) | 5-methyl-1-CH$_3$-indole | 478 | B |
| 61-(37) | 3-methyl-1-CH$_3$-indole | 478 | B |
| 61-(38) | 2-methylbenzothiophene | 481, 482 | B |
| 61-(39) | 3-methyl-1H-indazole | 466 | B |
| 61-(40) | 2-methyl-5-fluoro-1H-indole | 482, 484 | B |
| 61-(41) | 4,5-dimethyl-3-phenylisoxazole | 506, 507 | A |
| 61-(42) | 4-methylcinnoline | 477 | A |
| 61-(43) | 3-methyl-1H-pyrrole | 414 | B |
| 61-(44) | 4-methyl-3-phenyl-1H-pyrrole | 490, 491 | B |

EXAMPLE 62

General Procedure for the Amide Derivatives (5)

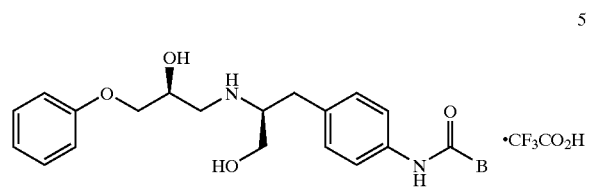

A mixture of a carboxylic acid derivative

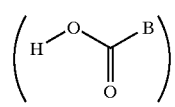

corresponding to an objective amide derivative (0.024 mmol) and 1.0 M pyridine in 1,2-dichloroethane (DCE) (24 µl) was treated with 1.0 M solution of oxallyl chloride in DCE (26 µl) at room temperature. After stirring for 1 hour, the mixture was diluted with N-methyl-2-pyrrolidinone (NMP) (20 µl). To a solution of tert-butyl N-[(1S)-1-(4-aminobenzyl)-2-hydroxyethyl]-N-[(2R)-2-hydroxy-3-phenoxypropyl]carbamate (0.02 mmol) in NMP (20 µl) was added 1.0 M solution of N,O-bis(trimethylsilyl)acetamide (BSA) in NMP (20 µl, 0.02 mmol), and the solution was stirred at room temperature. After stirring for 30 minutes, the solution was added to the acid chloride solution. After further stirring at 50° C. for 30 minutes, the reaction mixture was treated with 95% trifluoroacetic acid (TFA) in water (500 µl) at 50° C. for 30 minutes. The mixture was concentrated under reduced pressure and the residue was purified by HPLC (reverse phase $C_{18}$, 0–80% 0.1% TFA in acetonitrile/0.1% TFA in water). The fractions containing the desired compound were combined, concentrated and dried under reduced pressure to give the objective amide derivative (5).

Following the procedure outlined above, the compounds listed in Table 4 were obtained.

TABLE 4

| Example | B | MS [M + H]+ Data |
|---|---|---|
| 62-(1) | 4'-CF3-biphenyl-2-yl (via 2-methyl) | 565 |
| 62-(2) | 3-methylindol-1-yl-methyl substituent | 460 |
| 62-(3) | 3,4-dimethylisoxazol-5-yl | 440 |
| 62-(4) | 2-methyl-3-benzoylpyridin-yl | 526 |
| 62-(5) | 3-methylbiphenyl | 497 |
| 62-(6) | 2,4,5-trimethylthiazol-yl | 456 |
| 62-(7) | methyl-pyrrolo-indolone | 512 |
| 62-(8) | 2,3,7-trimethylindol-yl | 488 |

TABLE 4-continued

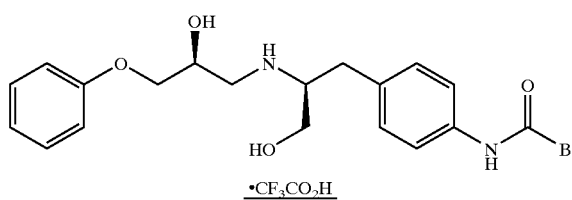
•CF$_3$CO$_2$H

| Example | B | MS [M + H]$^+$ Data |
|---|---|---|
| 62-(9) | 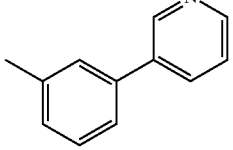 | 498 |
| 62-(10) | 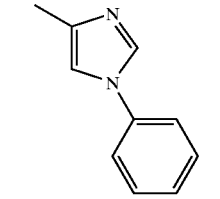 | 487 |
| 62-(11) | 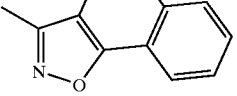 | 514 |
| 62-(12) | 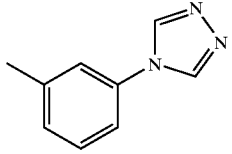 | 488 |
| 62-(13) | 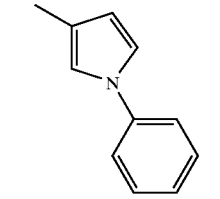 | 486 |
| 62-(14) | 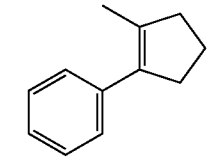 | 487 |
| 62-(15) | 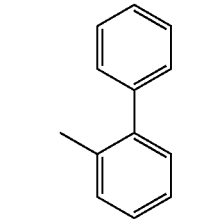 | 497 |

TABLE 4-continued

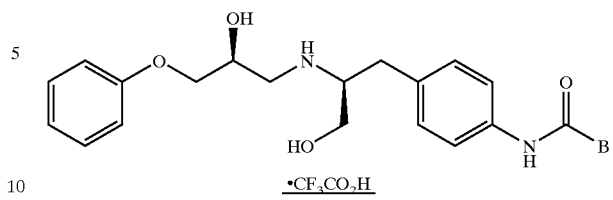
•CF$_3$CO$_2$H

| Example | B | MS [M + H]$^+$ Data |
|---|---|---|
| 62-(16) | 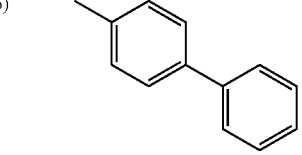 | 497 |

EXAMPLE 63

General Procedure for the Amide Derivatives (6)

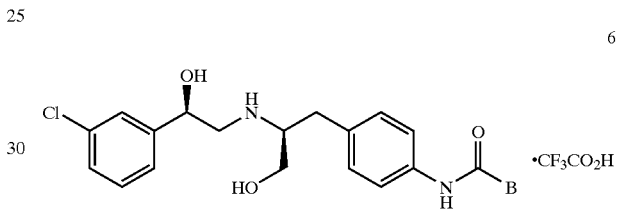

6

The amide derivatives above were obtained according to a similar manner to that of Example 62 using tert-butyl N-[(1S)-1-(4-aminobenzyl)-2-hydroxyethyl]-N-[(2R)-2-(3-chlorophenyl)-2-hydroxyethyl]carbamate instead of tert-butyl N-[(1S)-1-(4-aminobenzyl)-2-hydroxyethyl]-N-[(2R)-2-hydroxy-3-phenoxypropyl]carbamate.

Following the procedure outlined above, the compounds listed in Table 5 were obtained.

TABLE 5

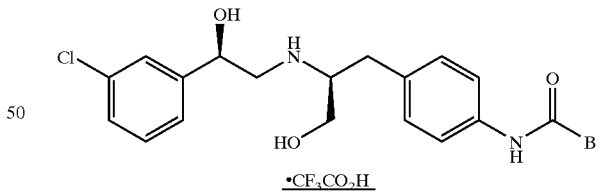
•CF$_3$CO$_2$H

| Example | B | MS [M + H]$^+$ Data |
|---|---|---|
| 63-(1) | 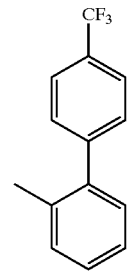 | 570 |

TABLE 5-continued

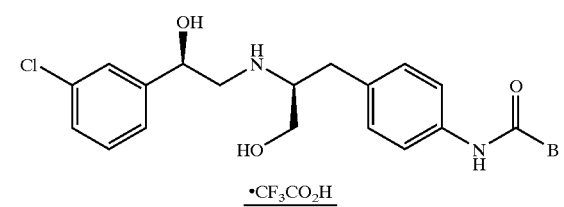
•CF₃CO₂H

| Example | B | MS [M + H]⁺ Data |
|---|---|---|
| 63-(2) | 3-methyl-1H-indole | 464 |
| 63-(3) | 4-methyl-5-methyl-1-phenyl-pyrazole | 506 |
| 63-(4) | 3,4,5-trimethylisoxazole | 444 |
| 63-(5) | 2-methyl-3-benzoylpyridine | 531 |
| 63-(6) | 3-methylbiphenyl | 502 |
| 63-(7) | 2,4,5-trimethylthiazole | 460 |
| 63-(8) | methyl-pyrrolo-indolone | 516 |

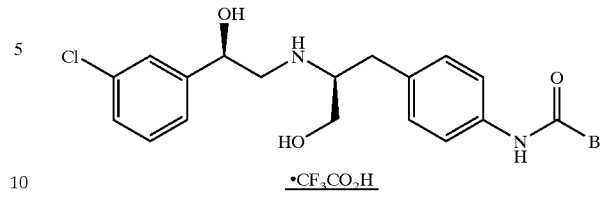
•CF₃CO₂H

| Example | B | MS [M + H]⁺ Data |
|---|---|---|
| 63-(9) | 2,3,7-trimethyl-1H-indole | 493 |
| 63-(10) | 3-(3-methylphenyl)pyridine | 503 |
| 63-(11) | 4-methyl-1-phenylimidazole | 491 |
| 63-(12) | 3-methyl-naphtho-isoxazole | 518 |
| 63-(13) | 3-methyl-1-phenylpyrrole | 490 |
| 63-(14) | 2-methyl-1-phenylcyclopentene | 492 |
| 63-(15) | 2'-methylbiphenyl | 502 |

TABLE 5-continued

Structure:

Cl-phenyl-CH(OH)-CH2-NH-CH(CH2OH)-CH2-C6H4-NH-C(=O)-B · CF3CO2H

| Example | B | MS [M + H]+ Data |
|---|---|---|
| 63-(16) | 4'-methylbiphenyl-4-yl | 502 |
| 63-(17) | 4-methyl-5-[4-(trifluoromethyl)phenyl]oxazol-2-yl | 560 |

EXAMPLE 64

General Procedure for the Urea Derivatives (7)

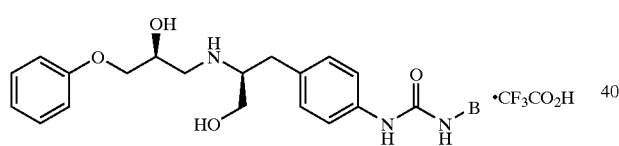

7

To a solution of tert-butyl N-[(1S)-1-(4-aminobenzyl)-2-hydroxyethyl]-N-[(2R)-2-hydroxy-3-phenoxypropyl] carbamate (0.02 mmol) in N-methyl-2-pyrrolidinone (NMP) (40 μl) was added 2.0 M solution of N,O-bis(trimethylsilyl) acetamide (BSA) in NMP (10 pl, 0.02 mmol) at room temperature. After stirring for 30 minutes, 1.0 M solution of an isocyanate derivative (O=C=N—B) corresponding to an objective urea derivative in NMP (24 pl, 0.024 mmol) and 0.1 M solution of N,N-diisopropylethylamine (DIEA) in NMP (20 μl, 0.002 mmol) were added to the solution. After further stirring at 50° C. for 30 minutes, the reaction mixture was treated with 95% trifluoroacetic acid (TFA) in water (500 μl) at 50° C. for 30 minutes. The mixture was concentrated under reduced pressure and the residue was purified by HPLC (reverse phase C18, 0–80% 0.1% TFA in acetonitrile/0.1% TFA in water). The fractions containing the desired compound were combined, concentrated and dried under reduced pressure to give the objective urea derivative (7).

Following the procedure outlined above, the compounds listed in Table 6 were obtained.

TABLE 6

Structure:

PhO-CH2-CH(OH)-CH2-NH-CH(CH2OH)-CH2-C6H4-NH-C(=O)-NH-B · CF3CO2H

| Example | B | MS [M + H]+ Data |
|---|---|---|
| 64-(1) | 4-methylphenyl | 450 |
| 64-(2) | 4-chlorophenyl | 470 |
| 64-(3) | 2-bromophenyl | 515 |
| 64-(4) | 2-methoxyphenyl | 466 |
| 64-(5) | 4-(trifluoromethyl)phenyl | 504 |
| 64-(6) | 4'-phenylbiphenyl-4-yl (biphenyl-4-yl, methyl substituent) | 512 |
| 64-(7) | 2'-methylbiphenyl-2-yl | 512 |
| 64-(8) | 2-phenoxyphenyl (methyl substituent) | 528 |

TABLE 6-continued

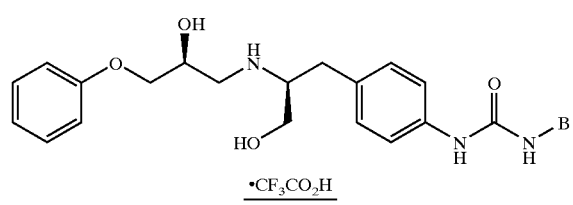
·CF₃CO₂H

| Example | B | MS [M + H]⁺ Data |
|---|---|---|
| 64-(9) | 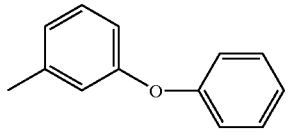 | 528 |
| 64-(10) | 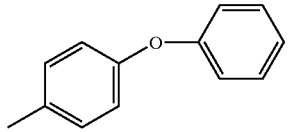 | 528 |
| 64-(11) | 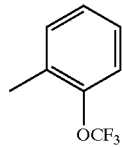 | 520 |
| 64-(12) | 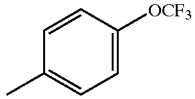 | 520 |
| 64-(13) | 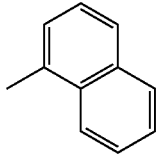 | 486 |
| 64-(14) | 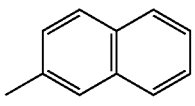 | 486 |
| 64-(15) | 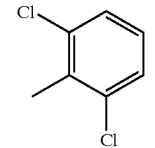 | 505 |

TABLE 6-continued

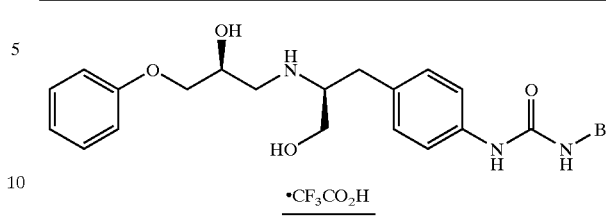
·CF₃CO₂H

| Example | B | MS [M + H]⁺ Data |
|---|---|---|
| 64-(16) | 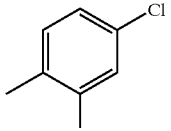 | 505 |
| 64-(17) | 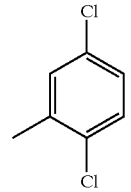 | 505 |

EXAMPLE 65

General Procedure for the Amide Derivatives (8)

8

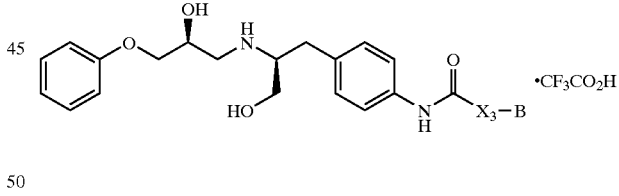

The amide derivatives above were obtained according to a similar manner to that of Example 64 using an acyl chloride derivative

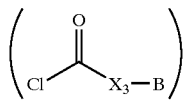

instead of an isocyanate derivative (O=C=N—B).

Following the procedure above, the compounds listed in Table 7 were obtained.

TABLE 7

Structure:
OH group, phenoxy-propanol linked via NH to a chiral center with CH2OH, connected to 4-substituted phenyl bearing NHC(O)NH-X3—B
·CF3CO2H

| Example | X3—B | MS [M + H]+ Data |
|---|---|---|
| 65-(1) | N-methyl-N-phenyl (with CH3) | 450 |
| 65-(2) | N-methylpiperidinyl | 428 |

EXAMPLE 66

General Procedure for the Urea Derivatives (9)

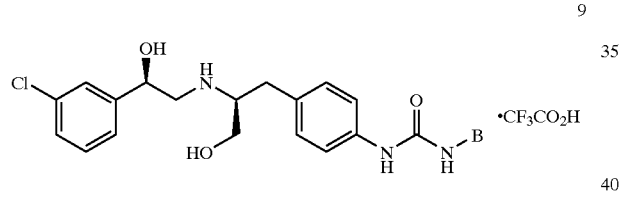

(9)
·CF3CO2H

To a solution of tert-butyl N-[(1s)-1-(4-aminobenzyl)-2-hydroxyethyl]-N-[(2R)-2-(3-chlorophenyl)-2-hydroxyethyl]-carbamate (0.02 mmol) in NMP (40 ul) was added 2.0 M solution of N,O-bis(trimethylsilyl)acetamide (BSA) in N-methyl-2-pyrrolidinone (NMP) (10 µl, 0.02 mmol) and the mixture was shaken for 30 minutes at room temperature. To the solution, 1.0 M solution of an isocyanate derivative (O=C=N—B) corresponding to an objective urea derivative in NMP (24 µl, 0.024 mmol) and 0.1 M solution of N,N-diisopropylethylamine (DIEA) in NMP (20 µl, 0.002 mmol) were added and the mixture was shaken for 30 minutes at 50° C. After cooling to room temperature, 0.5 ml of 95% trifluoroacetic acid (TFA) in water was added to the solution and shaken for 15 hours. The mixture was concentrated under reduced pressure and purified by HPLC (reverse phase $C_{18}$, 0–80% 0.1% TFA in acetonitrile/0.1% TFA in water). The fractions containing the desired compound were combined, concentrated and dried under reduced pressure to give the objective urea derivative (9).

Following the procedure outlined above, the compounds listed in Table 8 were obtained.

TABLE 8

Structure: 3-chlorophenyl-CH(OH)-CH2-NH-CH(CH2OH)-CH2-(4-phenyl)-NHC(O)NH-B
·CF3CO2H

| Example | B | MS [M + H]+ Data |
|---|---|---|
| 66-(1) | 2-chloro-toluene | 474 |
| 66-(2) | 3-chloro-toluene | 474 |
| 66-(3) | 4-chloro-toluene | 474 |
| 66-(4) | 2-methoxy-toluene | 470 |
| 66-(5) | 3-methoxy-toluene | 470 |
| 66-(6) | 4-methoxy-toluene | 470 |
| 66-(7) | n-propyl (CH3) | 406, 408 |
| 66-(8) | isopropyl (CH(CH3)2) | 406 |
| 66-(9) | ethylphenyl | 454, 456 |

EXAMPLE 67
General Procedure for the Amide Derivatives (10)

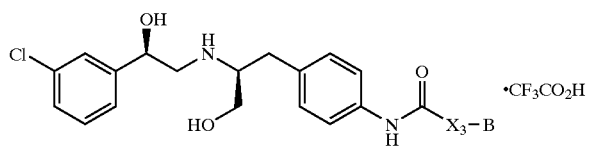

10

The amide derivatives above were obtained according to a similar manner to that of Example 66 using an acyl chloride derivative

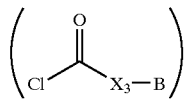

corresponding to an objective amide derivative instead of an isocyanate derivative (O=C=N—B).

Following the procedure above, the compounds listed in Table 9 were obtained.

TABLE 9

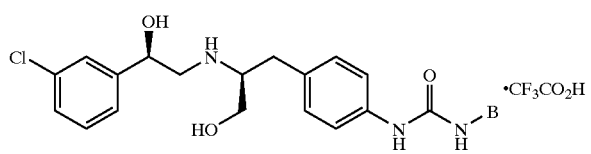

·CF$_3$CO$_2$H

| Example | X$_3$—B | MS [M + H]$^+$ Data |
|---|---|---|
| 67-(1) | *N,N-dimethylaniline group* | 454 |
| 67-(2) | *N-methylpiperidine group* | 432 |

EXAMPLE 68
General Procedure for the Urea Derivatives (11)

11

*[structure of compound 11 with ·CF$_3$CO$_2$H]*

To a 0.5 M solution of an amine derivative ($^H_H$N-B) corresponding to an objective urea derivative in N-methyl-2-pyrrolidinone (NMP) (50 μl, 0.025 mmol) was added 1.0 M solution of 1,1'-carbonyldiimidazole (CDI) (26.3 μl, 0.0263 mmol) and the mixture was shaken for 30 minutes at room temperature. In another vessel, a solution of tert-butyl N-[(1S)-1-(4-aminobenzyl)-2-hydroxyethyl-3-N-[(2R)-2-(3-chlorophenyl)-2-hydroxyethyl]carbamate (0.02 mmol) in NMP (20 μl) and 1.0 M solution of N,O-bis(trimethylsilyl)-acetamide (BSA) in NMP (20 μl, 0.02 mmol) was shaken for 30 minutes at room temperature, and the solution was added to the above solution. After shaking for 2 hours, 0.5 ml of 95% trifluoroacetic acid (TFA) in water was added to the solution and shaken for 15 hours. The mixture was concentrated under reduced pressure and purified by HPLC (reverse phase C$_{18}$, 0–80% 0.1% TFA in acetonitrile/0.1% TFA in water). The fractions containing the desired compound were combined, concentrated and dried under reduced pressure to give the objective urea derivative (11).

Following the procedure outlined above, the compounds listed in Table 10 were obtained.

TABLE 10

*[structure of urea derivative]*

| Example | B | MS [M + H]$^+$ Data |
|---|---|---|
| 68-(1) | *cyclohexyl* | 446 |
| 68-(2) | *3-methylpyridine* | 441, 442 |
| 68-(3) | *3-methylquinoline* | 491, 492 |
| 68-(4) | *6-methylquinoline* | 491 |
| 68-(5) | *5-methylisoquinoline* | 491, 493 |
| 68-(6) | *5-methylquinoline* | 491, 493 |
| 68-(7) | *1-methylisoquinoline* | 491, 492 |

What is claimed is:

1. A compound of the general formula [I]:

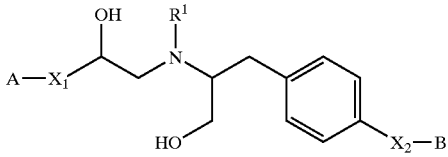

wherein

X₁ is bond or —O—CH₂—,

X₂ is 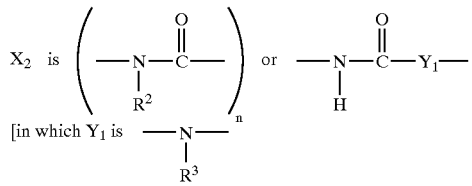

[in which Y₁ is 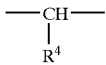

(in which R³ is hydrogen or lower alkyl),

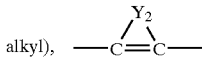

(in which R⁴ is hydrogen or lower alkyl), alkyl), —C=C—
      / Y₂ \

(in which Y₂ is lower alkylene)],

R¹ is hydrogen or an amino protective group,

A is phenyl, indolyl or carbazolyl, each of which may be substituted with one or two substituent(s) selected from the group consisting of halogen, hydroxy, hydroxy(lower)alkyl and benzyloxy, and B is hydrogen; halogen; lower alkyl; lower alkoxycarbonyl; cyclo(lower)alkyl; or a heterocyclic group, naphthyl, 1,2,3,4-tetrahydronaphthyl, benzyl or phenyl, each of which may be substituted with one or two substituent(s) selected from the group consisting of halogen, lower alkoxy, mono(or di or tri)halo(lower)alkoxy, carboxy(lower)alkoxy, lower alkoxycarbonyl (lower)alkoxy, phenoxy, lower alkyl, mono(or di or tri)halo(lower)alkyl, cyano, carboxy, lower alkoxycarbonyl, lower alkanoyl, benzoyl, mono(or di) (lower)alkylcarbamoyl, (lower alkylsulfonyl) carbamoyl, (lower alkylsulfonyl)-amino, (lower alkoxycarbonyl)amino, amino, nitro, pyridyl, triazolyl, thiazolyl optionally substituted with phenyl or lower alkyl, and phenyl optionally substituted with mono(or di or tri)halo(lower)alkyl, or a salt thereof.

2. A compound of claim 1, wherein

X₁ is bond or —O—CH₂—,

X₂ is 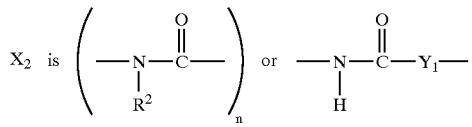

[in which

Y is 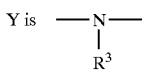

(in which R³ is hydrogen or lower alkyl),

—CH—
 |
 R⁴

(in which R⁴ is hydrogen or lower alkyl), alkyl), 

(in which Y₂ is lower alkylene)],

R¹ is hydrogen,

A is phenyl which may be substituted with one or two substituent(s) selected from the group consisting of halogen, hydroxy, hydroxy(lower)alkyl and benzyloxy, B is pyrrolyl, imidazolyl, pyrazolyl, pyridyl, pyrazinyl, piperidyl, indolyl, benzimidazolyl, quinolyl, isoquinolyl, quinoxalinyl, cinnolinyl, indazolyl, oxazolyl, isoxazolyl, thiazolyl, thienyl, furyl, benzofuranyl, benzothienyl, naphthyl, benzyl or phenyl, each of which may be substituted with one or two substituent(s) selected from the group consisting of halogen, lower alkoxy, mono(or di or tri)halo(lower) alkoxy, carboxy(lower)alkoxy, lower alkoxycarbonyl-(lower)alkoxy, phenoxy, lower alkyl, mono(or di or tri)halo(lower)alkyl, cyano, carboxy, lower alkoxycarbonyl, lower alkanoyl, benzoyl, mono(or di) (lower)alkylcarbamoyl, (lower alkylsulfonyl)-carbamoyl, (lower alkylsulfonyl)amino, (lower alkoxycarbonyl)amino, amino, nitro, pyridyl, triazolyl, thiazolyl optionally substituted with phenyl or lower alkyl, and phenyl optionally substituted with mono(or di or tri)halo(lower)alkyl.

3. A compound of claim 2, wherein

X₁ is —O—CH₂—,

X₂ is 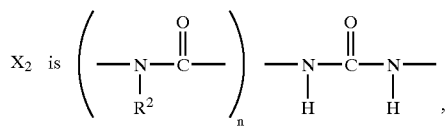

R¹ is hydrogen,

A is phenyl which may be substituted with one or two substituent(s) selected from the group consisting of halogen, hydroxy, hydroxy(lower)alkyl and benzyloxy, B is pyrrolyl, pyridyl, naphthyl or phenyl, each of which may be substituted with one or two substituent(s) selected from the group consisting of halogen, lower alkoxy, carboxy(lower)alkoxy, lower alkoxycarbonyl (lower)alkoxy, lower alkyl, mono(or di or tri)halo (lower)alkyl, cyano, carboxy, lower alkoxycarbonyl, lower alkanoyl, mono(or di)(lower)alkylcarbamoyl, (lower alkylsulfonyl)carbamoyl, (lower alkylsulfonyl) amino, (lower alkoxycarbonyl) amino and nitro.

4. A compound of claim 3, which is (1) N-[4-[(2S)-3-hydroxy-2-[[(2S)-2-hydroxy-3-phenoxypropyl]amino]propyl]phenyl]-1H-pyrrole-2-carboxamide;

(2) N-[4-[(2S)-3-hydroxy-2-[[(2S)-2-hydroxy-3-phenoxypropyl]amino]propyl]phenyl]-N'-phenylurea;

(3) N-[4-[(2S)-3-hydroxy-2-[[(2S)-2-hydroxy-3-phenoxypropyl]amino]propyl]phenyl]-1-naphthamide;

(4) N-(3-fluorophenyl)-N'-[4-[(2S)-3-hydroxy-2-[[(2S)-2-hydroxy-3-phenoxypropyl]amino]propyl]phenyl]urea;

(5) N-[4-[(2S)-3-hydroxy-2-[[(2S)-2-hydroxy-3-phenoxypropyl]amino]propyl]phenyl]-N'-(3-methoxyphenyl)urea, or a salt thereof.

5. A process for preparing a compound of claim 1, or a salt thereof, which comprises, (i) reacting a compound [II] of the formula:

[II]

wherein $X_1$ and A are each as defined in claim 1, or a salt thereof, with a compound [III] of the formula:

[III]

wherein $X_2$, $R^1$ and B are each as defined in claim 1, or a salt thereof, to give a compound [I] of the formula:

[I]

wherein $X_1$, $X_2$, $R^1$, A and B are each as defined in claim 1, or a salt thereof, or (ii) subjecting a compound [Ia] of the formula:

[Ia]

wherein $X_1$, $X_2$, A and B are each as defined in claim 1, and $R_a^1$ is an amino protective group, or a salt thereof, to elimination reaction of the amino protective group, to give a compound [Ib] of the formula:

[Ib]

wherein $X_1$, $X_2$, A and B are each as defined in claim 1, or a salt thereof, or (iii) reacting a compound [IV] of the formula:

[IV]

wherein $X_1$, $R^1$ and A are each as defined in claim 1, or a salt thereof, with a compound [V] of the formula:

[V]

wherein B is as defined in claim 1, and $W_1$ is a leaving group, or a salt thereof, to give a compound [Ic] of the formula:

[Ic]

wherein $X_1$, $R^1$, A and B are each as defined in claim 1, or a salt thereof, or (iv) reacting a compound [Id] of the formula:

[Id]

wherein $X_1$, $R^1$, A and B are each as defined in claim 1, and m is an integer of 1 or 2, or a salt thereof, with a compound [VI] of the formula:

$$W_2-R_a^2$$ [VI]

wherein $R_a^2$ is lower alkyl, and $W_2$ is an acid residue, to give a compound [Ie] of the formula:

[Ie]

wherein $X_1$, $R^1$, A and B are each as defined in claim 1, $R_a^2$ is lower alkyl, and m is an integer of 1 or 2, or a salt thereof, and (v) reacting a compound [IV] of the formula:

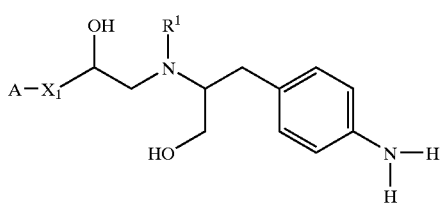

[IV]

wherein $X_1$, $R^1$ and A are each as defined in claim 1, or a salt thereof, with a compound [VII] of the formula:

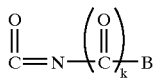

[VII]

wherein B is as defined in claim 1, and k is 0 or an integer of 1, or a salt thereof, to give a compound [If] of the formula:

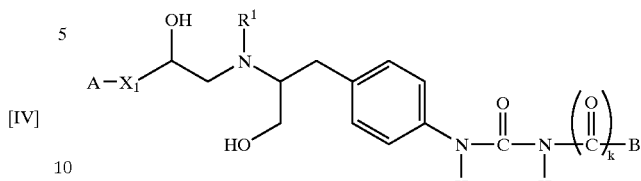

[If]

wherein $X_1$, $R^1$, A and B are each as defined in claim 1, and k is 0 or an integer of 1, or a salt thereof.

6. A pharmaceutical composition which comprises, as an active ingredient, a compound of claim 1 or a pharmaceutically acceptable salt thereof in admixture with pharmaceutically acceptable carriers or excipients.

7. Use of a compound of claim 1 or a pharmaceutically acceptable salt thereof for the manufacture of a medicament.

8. A compound of claim 1 or a pharmaceutically acceptable salt thereof for use as a medicament.

9. A method for the prophylactic and/or therapeutic treatment of pollakiuria, urinary incontinence, obesity or diabetes, which comprises administering a compound of claim 1 or a pharmaceutically acceptable salt thereof to a human being or an animal.

* * * * *